US006395501B1

(12) United States Patent
Rosén et al.

(10) Patent No.: US 6,395,501 B1

(45) Date of Patent: May 28, 2002

(54) IN VITRO METHODS FOR SCREENING FOR BLOOD COAGULATION DISORDERS USING METAL IONS

(75) Inventors: Bert Steffen Rosén, Kållered; Christina Maria Yvonne Hall, Onsala, both of (SE)

(73) Assignee: Instrumentation Laboratory, S.p.A., Milan (IT)

( * ) Notice: Subject to any disclaimer, the term of this patent is extended or adjusted under 35 U.S.C. 154(b) by 0 days.

(21) Appl. No.: 09/273,413

(22) Filed: Mar. 19, 1999

(30) Foreign Application Priority Data

Mar. 19, 1998 (EP) ........................................... 98105043

(51) Int. Cl.[7] ................................................. C12Q 1/56

(52) U.S. Cl. ........................................... 435/13; 436/69

(58) Field of Search ............................... 435/13; 436/69

(56) References Cited

U.S. PATENT DOCUMENTS

| | | | | |
|---|---|---|---|---|
| 5,001,069 A | * | 3/1991 | Bartl et al. | 436/86 |
| 5,055,412 A | | 10/1991 | Proksch | 436/69 |
| 5,439,802 A | * | 8/1995 | Rosen | 435/13 |
| 5,637,452 A | | 6/1997 | Speck | 435/4 |
| 5,637,492 A | * | 6/1997 | Dawson et al. | 435/217 |

FOREIGN PATENT DOCUMENTS

| | | | |
|---|---|---|---|
| WO | WO 93/10262 | | 5/1993 |
| WO | WO 99/41615 | * | 8/1999 |

OTHER PUBLICATIONS

Gable P. Protac . . . Thrombosis Research 86(1)79–84, Jan. 1997.*

Bernado et al.: Surface–independent Acceleration of Factor XII Activation by Zinc Ions, *J. Biol. Chem.* 268(17):12468–12476 (1993).

Butenas et al.: Cooperative Interaction of Divalent Metal Ions, Substrate, and Tissue Factor with Factor VIIa, *J. Biol. Chem.* 33:3449–3456 (1994).

Liebman et al.: The Factor IX Phospolipid–binding Site Is Required for Calcium–dependent Activation of Factor IX by Factor Xia, *J. Biol. Chem.* 262(16):7605–7612 (1987).

Heeb et al.: Identification of divalent metal ion–dependent inhibition of activated protein C by alpha 2–macroglobulin and alpha 2–antiplasmin in blood and comparisons to inhibition of factor Xa, thrombin, and plasmin, *J. Biol. Chem* 266(26):17606–17612 (1991).

Sekiya et al.: Regulation of Tertiary Structure and Function of Coagulation Factor IX by Magnesium (II) Ions*, *J. Biol. Chem.* 270(24):14325–14331 (1995).

Shore et al.: Acceleration of Surface–Dependent Autocatalytic Activation of Blood Coagulation Factor XII by Divalent Metal Ions, *J. Biol. Chem.* 26: 2250–2258 (1987).

Pedersen et al.: Inhibition of Recombinant Human Blood Coagulation Factor VIIa Amidolytic and Proteolytic Activity by Zinc Ions, *Thrombosi and Haemostasis* 65(5):528–534 (1991).

Patent Cooperation Treaty, International Search Report, International Application No. PCT/EP 99/01599, mailed on Jul. 27, 1999, 8 pages.

* cited by examiner

*Primary Examiner*—Ralph Gitomer

(74) *Attorney, Agent, or Firm*—Testa, Hurwitz & Thibeault, LLP

(57) ABSTRACT

In vitro methods for qualitative screening and quantitative determination of the functional activity of components of the Protein C anticoagulant pathway of the blood coagulation system are provided. The methods entail providing a blood sample to be analyzed, activating the coagulation cascade, triggering coagulation by adding calcium ions, adding metal ions selected from the group consisting of divalent metal ions and monovalent copper ions at a concentration that enhances the anticoagulant activity of the Protein C anticoagulant pathway, adding an exogenous substrate for an enzyme related to Protein C anticoagulant activity, measuring the conversion rate of a the exogenous substrate by the enzyme, and comparing the conversion rate of the substrate in blood sample to be analyzed with the conversion rate the substrate in a normal blood sample.

50 Claims, 8 Drawing Sheets

6.6 mM Ca2+
6.6 mM Ca2+ + 0.04 mM Mn2+
DO 405-490nm
1.5
1
0.5
0
0
20
40
60
80
100
% Free Protein S 0% Prot C
0% Prot S
FV: R506Q
FV: Q506
Delta Abnormal - Normal
1
0.5
0
6.6 mM $Ca^{2+}$
6.6 mM $Ca^{2+}$ +
0.4 mM $Mg^{2+}$ +
0.04 mM $Mn^{2+}$

IN VITRO METHODS FOR SCREENING FOR BLOOD COAGULATION DISORDERS USING METAL IONS

RELATED APPLICATION

This application claims priority to European Pat. Appln. 98 105 043.8, filed Mar. 19, 1998.

FIELD OF THE INVENTION

The present invention relates to in vitro methods, kits and reagents for the qualitative screening and quantitative determination of the functional activity of components of the Protein C anticoagulant pathway of blood coagulation.

BACKGROUND OF THE INVENTION

Maintenance of proper hemostasis is the result of a careful balance between procoagulant and anticoagulant activities. After a trauma, coagulation is triggered primarily through activation of coagulation Factors IX and X (FIX, FX) by tissue factor (also denoted tissue thromboplastin) and Factor VII (FVII) followed by generation of thrombin, which in turn cleaves fibrinogen to form soluble fibrin. After crosslinking by Factor XIII, a three-dimensional insoluble gel clot is obtained which prevents further blood losses.

Regulation of this highly potent system, shown schematically in FIG. 1, is accomplished by a balanced relation between procoagulant activities (shown with solid line arrows) and anticoagulant activities (shown with dashed line arrows). The anticoagulant activities include (1) inhibition of thrombin by antithrombin (AT) and $\alpha_2$-macroglobulin, and (2) prevention of further thrombin formation by the Protein C anticoagulant pathway. In that pathway, activated Protein C (APC) inactivates the coagulation proteins Factor VIII and Factor V in their activated forms (FVIIIa, FVa) through proteolytic cleavage. In addition, Factor Xa is inhibited by antithrombin and tissue factor pathway inhibitor (TFPI), the latter also inhibiting the tissue factor/Factor VIIa complex. Factor VIIa and Factor Va have potent procoagulant activities as cofactors in the activation of Factor X and prothrombin, respectively, and increase the reaction rates of these processes about 1000-fold each. Therefore, the inactivation of Factors Va and VIIIa by APC essentially stops further thrombin generation, thus providing a strong anticoagulant effect. Protein S and Factor V act as cofactors to activated Protein C (APC).

As shown in FIG. 1, the activation of coagulation through the intrinsic or extrinsic systems results in the activation of Factor X, a key component in the final common pathway. In the intrinsic system, the initial event is the activation of contact factors (Factor XII, prekallikrein) followed by the activation of Factor XI, which in turn activates Factor IX. In the extrinsic system, Factor IX and Factor X are activated by the tissue factor/Factor VIIa complex.

As FIG. 1 shows, calcium ions have to be present in several of these reactions. The activation of Factor X by Factor IXa, and of prothrombin by Factor Xa, also requires procoagulant phospholipids. In vivo, this is provided by the membrane surface of activated platelets; in vitro by platelet extracts, purified phospholipids, synthetic phospholipids and/or crude phospholipid extracts from suitable sources. The total and free calcium ion concentrations in native plasma are about 2.4 and 1.2 mmol/L, respectively. Typically, calcium ion concentrations used in analytical methods for the determination of coagulation or anticoagulation factors are in the range 1.5–10 mmol/L. The concentrations of other metal ions in plasma are lower, with typical values for the total concentration being 1 mmol/L for $Mg^{2+}$ and 5–40 $\mu$mol/L for $Zn^{2+}$, $Cu^{2+}$ and $Mn^{2+}$.

Defects in the Protein C anticoagulant pathway may increase the risk of thrombosis due to a decreased capacity to prevent thrombin formation. Such defects may be due to deficiencies in the activity of Protein C and/or its cofactor Protein S. Another recently detected defect is a point mutation in the Factor V gene (G→A) at nucleotide 1691, resulting in the amino acid substitution Arg (R)→Gln (Q) at position 506 in Factor V/Factor Va, denoted FV:$Q^{506}$ or Factor V Leiden. Heterozygosity and homozygosity for this mutation are often denoted FV:R506Q and FV:Q506Q, respectively. This mutation is at one of the three APC cleavage sites (amino acids 306, 506, 679) in Factor Va, impairs its degradation by activated Protein C (APC), and confers a condition denoted as APC resistance.

APC resistance is to be considered a blood coagulation disorder recognized by an abnormally low anticoagulant response to activated Protein C (APC), and the determination of APC resistance may be used to screen for and diagnose thromboembolic diseases, such as hereditary thrombophilia, or for determining the risk for a human to acquire a manifestation of this blood coagulation disorder (e.g., European Pat. No. 608235).

Hence, there is a need to investigate these components of the Protein C anticoagulant pathway in the evaluation of thrombotic patients, and potentially also to screen for abnormalities of Protein C, Protein S and Factor V anticoagulant activity in situations connected with an increased risk of thrombosis, such as before surgery, during and after trauma, during pregnancy, or in connection with the use of oral contraceptive pills or hormone replacement therapy. Currently, clotting and/or chromogenic assays are available for analysis of Protein C and Protein S activity as well as for the detection of APC resistance (at least 90% of which is due to the FV:$Q^{506}$ mutation).

Protein C activity is typically measured after activation of endogenous Protein C, contained in a plasma sample, by thrombin or by a snake venom enzyme from *Agkistrodon contortrix contortrix* (e.g., European Patent 203509 to Stocker), commercially available as the reagent Protac®C (Pentapharm AG, Basel, Switzerland). The concentration of Protac®C in the activation mixture is typically about 0.1 U/mL or higher since otherwise an insufficient activation of Protein C may be obtained (Martinoli et al. (1986), *Thromb. Res.* 43:253–264; McCall et al. (1987), *Thromb. Res.* 45:681–685).

After activation by Protac®C, the protein C activity is determined with a clotting or chromogenic assay (Bertina (1990), *Res. Clin. Lab.* 20:127–138; Marlar et al. (1989), *Hum. Pathol.* 20:1040–1047; European Pat. No. 486515). In clotting methods, coagulation is triggered through the intrinsic pathway by using APTT reagents or through the extrinsic pathway with the use of tissue factor. In both cases calcium ions are added to a final concentration of usually 5–10 mmol/L. Commercial kits and reagents are available for the determination of Protein C activity, such as Acticlot™ C (American Diagnostica GmbH, Pfungstadt, Germany), Stachrom Protein C (Diagnostica Stago, Asnières, France), Staclot Protein C (Diagnostica Stago, Asnières, France), Coamatic® Protein C (Chromogenix AB, Mölndal, Sweden) and Protein C Activator (Dade Behring, Deerfield, Ill.).

The activation of Protein C by thrombin is stimulated about 1000-fold by thrombomodulin, an endothelial cell membrane protein (Esmon et al. (1981), *Proc. Natl. Acad.*

*Sci.* (*USA*) 78:2249–2252). The use of thrombin/thrombomodulin as activator of Protein C for analysis of Protein C and/or Protein S activity in plasma samples, utilizing a photometric method, is also known (French Pat. Appln. No. 2689 640-A1).

Protein S activity is determined from its stimulation of the activity of APC in its degradation of Factor Va and/or Factor VIIIa. Typically, in such assays a standardized amount of APC is added to a plasma sample or activation of endogenous protein C is performed whereafter the clotting time is determined after a simultaneous or separate coagulation activation via the intrinsic system using an APTT reagent, via the extrinsic system using tissue factor or Factor Xa (Bertina (1990), supra; Preda et al. (1990), *Thromb. Res.* 60:19–32; D'Angelo et al. (1995), *Thromb. Res.* 77:375–378). Chromogenic activity assays for protein S have also been published, utilizing Factor IXa as an activator and monitoring Factor Xa generation (European Pat. No. 567 636) or thrombin generation (European Pat. No. 486 515). In all these methods, calcium ions are added as mentioned above.

The FV:$Q^{506}$ mutation in the Factor V molecule may be detected with molecular biology methods based upon the use of the polymerase chain reaction (PCR) technique (Bertina et al. (1994), *Nature* 369:64–67), or by methods in which the functional activity of APC is determined. Such functional activity methods may be coagulation-based (e.g., European Pat. No. 608235; Rosén et al. (1994), *Thromb. Haemost.* 72:255–260), and may include the use of predilution of sample plasma with a plasma with little or no Factor V activity (European Pat. Appln. No. EP-A-94 905 908.3; Jorquera et al. (1994), *Lancet* 344:1162–1163; Svensson et al. (1997), *Thromb. Haemost.* 77:332–335). The latter assay principle, a coagulation-based assay using predilution of sample plasma, is also utilized in a commercial product, Coatest® APC Resistance V (Chromogenix AB). Alternatively, chromogenic methods may be used (European Pat. No. 608 235; Rosén et al. (1995), *Thromb. Haemost.* 73:1364, Abstract 1778; Nicolaes et al. (1996), *Thromb. Haemost.* 76:404–410).

Since genetic defects in the Protein C anticoagulant pathway are found in about 25% of unselected patients with venous thromboembolism (VTE) and in about 50% of patients with thrombophilia (i.e., patients from families with an increased tendency to VTE), there is a need for a single test which detects all such abnormalities with a high sensitivity and specificity, i.e., a global (overall) test. One concept for a global test is based upon the activation of Protein C in plasma with Protac®C and activation of coagulation via the intrinsic or extrinsic pathway (U.S. Pat. No. 5,001,069; European Pat. Appln. No. 696 642). Results obtained with a commercial kit application of this test, ProC Global (Behring Diagnostica, Marburg, Germany), in which intrinsic activation of coagulation is accomplished through addition of an APTT reagent, show a sensitivity for Protein C deficiency, Protein S deficiency, and the FV:$Q^{506}$ mutation of, respectively, about 90%, 50–80% and more than 90% on analysis of healthy individuals and thrombotic patients (Dati et al. (1997), *Clin. Chem.* 43:1719–1723; Ruzicka et al. (1997), *Thromb. Res.* 87:501–510). The specificity, however, is about 50% in thrombotic cohorts and, therefore, a substantial proportion of positive results are obtained which can not be linked to known defects in components of the Protein C anticoagulant pathway, such as in protein C, protein S and Factor V. Thus, this test lacks sufficient specificity.

Furthermore, results from analysis of pregnant women lacking any of the known defects in the Protein C anticoagulant pathway are clearly different from analysis of normal healthy individuals (Rangård et al. (1997), *Annals Hematol.* 74, Supplement II, Abstract 74, A77; Siegemund et al. (1997), *Annals Hematol.* 74, Supplement II, Abstract 188, A105), which necessitates separate ranges for these cohorts. This as yet uncharacterized interference limits the general applicability of the test. An alternative global method for the detection of defects in the protein C anticoagulant pathway, based upon activation of endogenous plasma Protein C by Protac®C utilizes tissue factor as the trigger ofthe coagulation (Preda et al. (1996), *Blood Coag. Fibrinol.* 7:465–469). The sensitivity of this method also is limited, especially for Protein S. Furthermore, different sample categories, e.g., pregnant and non-pregnant women, may require different approaches for evaluation of the results due to interference from factors not related to known defects of the Protein C anticoagulant pathway.

For a global test to be useful as a screening test for known inherited defects in the Protein C anticoagulant pathway (e.g., Protein C deficiency, protein S deficiency or the FV:$Q^{506}$ mutation), the sensitivity should be high, at least 90%, for all these defects. Furthermore the specificity should be high, above 60%, preferably above 70%, and more preferably above 80%, in order to considerably reduce the number of false positive results. The state-of-the-art methods do not provide a satisfactory solution to these requirements. For the development of improved methods for the specific determination of Protein C and Protein S activity, and for determination of mutations in Factor V which affect its anticoagulant activity, it is also desirable to improve the resolution and specificity of these methods. There is also a need to improve the stability of different reagents used in such methods.

Thus, the technical problem underlying the present invention is the provision of in vitro methods with improved sensitivity and specificity for diagnostic screening and for the specific detection of defects in the Protein C anticoagulant pathway in humans. A further recognized problem is to improve the stability of reagents used in such methods.

SUMMARY OF THE INVENTION

The present invention is based, in part, upon the surprising finding that the addition of low levels of divalent metal ions, such as $Mg^{2+}$, $Mn^{2+}$, $Zn^{2+}$, $Ni^{2+}$, $Sr^{2+}$, or $Cu^{2+}$ ions, or of the monovalent copper ion (Cu+), in the presence of calcium ions, enhances the anticoagulant activity of the Protein C anticoagulant pathway, provides for a high degree of resolution between different levels of Protein C activity and Protein S activity, provides a high degree of discrimination for the presence of the FV:$Q^{506}$ mutation, and results in an improved sensitivity and specificity for detection of defects in components of the Protein C anticoagulant pathway with photometric and/or clotting methods. Thus, the invention also constitutes a "global" method for detecting defects in the Protein C anticoagulant pathway. In addition, the addition of divalent metal ions provides for an unexpected improvement of the stability of the reagents typically used in determining the anticoagulant activity of components of the Protein C anticoagulant pathway.

Thus, in one aspect, the present invention provides an in vitro method for qualitative screening and quantitative determination of the functional activity of components of the Protein C anticoagulant pathway of blood coagulation, comprising measuring the conversion rate of an exogenous substrate by an enzyme, the activity of which is related to Protein C anticoagulant activity, in a human blood or plasma sample comprising coagulation factors and said exogenous substrate, after at least partial activation of coagulation through the intrinsic, extrinsic or common pathways and triggering coagulation by adding calcium ions; and comparing said conversion rate with the conversion rate of a normal human blood or plasma sample determined in the same way, said method being characterized by adding further metal(s) ions to said sample.

The present invention is thus concerned with in vitro methods for screening for, in a human, defects in the Protein C anticoagulant pathway due to, for example, Protein C deficiency, Protein S deficiency, or Factor V mutations such as the FV:$Q^{506}$ mutation, or other Factor V defects related to APC resistance and/or APC cofactor activity. Such methods may be designed for the specific detection of Protein C deficiency, Protein S deficiency, or mutations in Factor V/Factor Va which affect the cleavage rate by APC. One preferred embodiment of the present invention comprises a global test for the Protein C anticoagulant pathway.

The methods of the invention allow improved screening and diagnosis of defects in the Protein C anticoagulant pathway in patients with thromboembolic diseases such as deep venous thrombosis and/or pulmonary embolism. In cases where a patient belongs to a family with hereditary thrombophilia, the methods are also suitable for the investigation of family members of the patient to determine the possible inheritance of defects within the pathway. The methods are also particularly useful for diagnosing defects in the Protein C anticoagulant pathway in patients before surgery, patients with trauma, in pregnant women, or in women receiving oral contraceptive pills or hormone replacement therapy such as estrogen therapy. Furthermore, the "global" methods of the invention may be used for the detection not only of known defects in the Protein C anticoagulant pathway, but also of hitherto unrecognized defects. In particular, the invention provides for specific photometric and/or clotting methods for such unrecognized defects in the Protein C anticoagulant pathway.

The methods of the invention may comprise monitoring the conversion of an exogenous photometric substrate for either Factor Xa or thrombin, containing a chromophore, fluorophore or luminophore as a leaving group. Examples of such photometrically measurable leaving groups are p-nitroaniline (a chromophore) for use in colorimetric methods; naphthylamine and coumarin derivatives such as methylcoumarine, aminoisophthalic acid and its derivatives (fluorophores) for use in fluorimetric methods; and isoluminolamide (a luminophore) for use in luminometric methods.

DETAILED DESCRIPTION OF THE INVENTION

Definitions

In order to more clearly and concisely describe and point out the subject matter of the claimed invention, the following definitions are provided for specific terms which are used in the following written description and the appended claims.

As used herein, the term "additional metal ions" refers to divalent metal ions, such as $Mg^{2+}$, $Mn^{2+}$, $Zn^{2+}$, $Ni^{2+}$, $Sr^{2+}$, or $Cu^{2+}$, to monovalent copper ions ($Cu^{+}$), or to mixtures thereof. These additional metal ions may be used in the methods and products of the invention in addition to the $Ca^{2+}$ ions which are typically used in such methods and products.

As used herein, the term "blood sample" is defined to cover a blood sample, such as whole blood, or a blood derived sample, such as a blood plasma sample or a blood serum sample.

As used herein, the term "photometric assay" is defined to include colorimetric, fluorimetric and luminometric assay methods.

Figure 1:
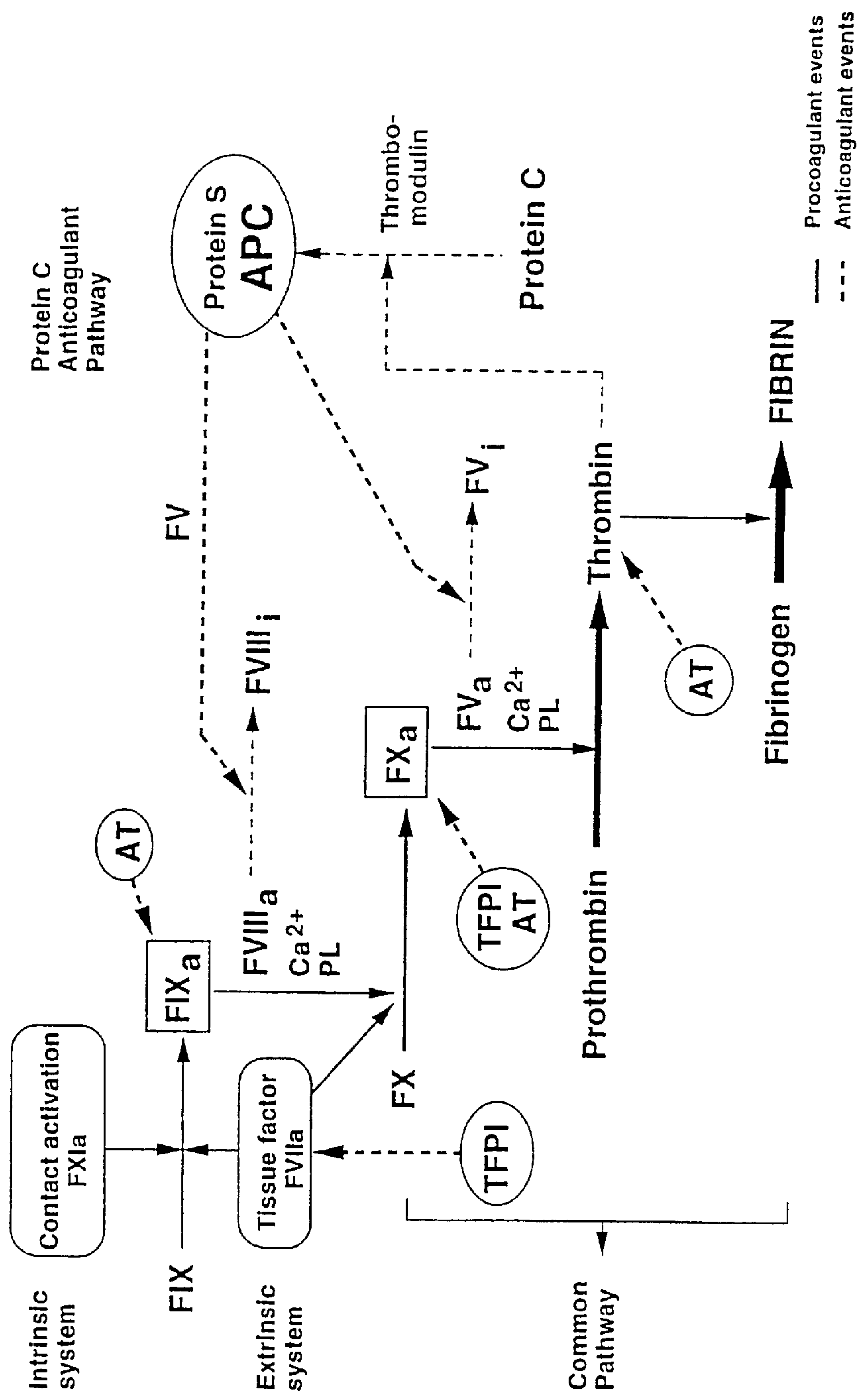
FIG. 1 is a schematic representation of the blood coagulation system and its regulation.

As used herein, the term "coagulation factors" refers to the factors of the blood coagulation pathway comprising components in the intrinsic, extrinsic and common coagulation pathways (procoagulant events see FIG. 1), or in the Protein C anticoagulant pathway (anticoagulant events see FIG. 1). The term embraces such factors whether they are present in a sample as endogenous components (i.e., being inherent in the blood sample), or whether they have been added as exogenous factors. Phospholipid(s) may also be included as coagulation factors when added in a method utilizing any of the intrinsic, extrinsic or common pathways for activation of coagulation.

The present invention is based, in part, upon the surprising finding that the addition of low levels of divalent metal ions, such as $Mg^{2+}$, $Mn^{2+}$, $Zn^{2+}$, $Ni^{2+}$, $Sr^{2+}$, or $Cu^{2+}$ ions, or of the monovalent copper ion ($Cu^{+}$), in the presence of calcium ions, enhances the anticoagulant activity of the Protein C anticoagulant pathway, provides for a high degree of resolution between different levels of Protein C activity and Protein S activity, provides a high degree of discrimination for the presence of the FV:$Q^{506}$ mutation, and results in an improved sensitivity and specificity for detection of defects in components of the Protein C anticoagulant pathway with photometric and/or clotting methods.

The present invention is most unexpected in light of the prior art, which teaches that several divalent ions increase the procoagulant activity of certain vitamin K-dependent coagulation factors in the presence of calcium ions (see procoagulant events in FIG. 1). Therefore, it would not be expected that the addition of such metal ions could improve tests relating to anticoagulant activity, and specifically to the Protein C anticoagulant pathway.

Thus, for example, it was known that $Mg^{2+}$ stimulates the activity of Factor IXa and also enhances the activation rate of Factor IX by Factor XIa and tissue factor (Byrne et al. (1980), *J. Biol. Chem.* 255:1430–1435; Sekiya et al. (1995), *J. Biol. Chem.* 270:14325–14331; Sekiya et al. (1996), *J. Biol. Chem.* 271:8541–8544; Morita et al. (1997), *Thromb. Haemost.* 78, Supplement 430, Abstract PS-1755). It was also shown that Protein C, prothrombin, Factor VII and Factor X are not responsive to $Mg^{2+}$ (Sekiya et al. (1995), supra). $Mg^{2+}$ also has been shown to stimulate prothrombin activation by Factor Xa, phospholipid and calcium ions (Prendergast et al. (1997), *J. Biol. Chem.* 252: 840–850), an effect which, however, may not be pronounced at calcium ion concentrations above 1 mmol/L (Sekiya et al. (1995), supra). Furthermore, it has been shown that Factor IX has a unique binding site for $Mn^{2+}$ (Amphlett et al. (1978), *J. Biol. Chem.* 253:6774–6779), which site has been suggested to be identical with the $Mg^{2+}$ binding site (Sekiya et al. (1995), supra). $Mn^{2+}$ ions have also been shown to enhance the binding of Factor IX to procoagulant phospholipids in the presence of calcium or $Sr^{2+}$ ions, the latter thus also having a procoagulant effect (Liebman et al. (1987), *J. Biol. Chem.* 262:7605–7612).

Furthermore, $Mg^{2+}$ and $Mn^{2+}$ ions have been shown to increase the amidolytic activity of Factor VIIa, i.e., the cleavage rate of low molecular weight synthetic peptide substrates (Butenas et al. (1994), *Biochemistry* 33:3449–3456; Persson et al. (1995), *Eur. J. Biochem.* 234:293–300), whereas $Zn^{2+}$ ions have been reported to have an inhibitory effect on the amidolytic activity of Factor VIIa but no effect on the amidolytic activity of Factor Xa, thrombin or activated Protein C (Pedersen et al. (1991), *Thromb. Haemost.* 65:528–534). $Mn^{2+}$ ions have also been shown to substitute for calcium ions in the activation of Factor X by Russell's Viper Venom enzyme, albeit providing a lower activation rate (Bajaj et al. (1977), *J. Biol. Chem.* 252:4758–4761).

The prior art also teaches that divalent metal ions such as $Zn^{2+}$ and $Cu^{2+}$ stimulate the autoactivation of Factor XII, a non-vitamin K-dependent coagulation factor (Shore et al. (1987), *Biochemistry* 26:2250–2258; Bernardo et al. (1993), *J. Biol. Chem.* 268:12468–12476).

In addition, the prior art teaches that $Mg^{2+}$ and $Mn^{2+}$ stimulate the inhibition of APC by the two plasma protease inhibitors $\alpha_2$-macroglobulin and plasmin inhibitor (Heeb et al. (1991), *J. Biol. Chem.* 266:17606–17612). Thus, the addition of $Mg^{2+}$ and $Mn^{2+}$ under the conditions used results in a decreased anticoagulant activity of APC.

Therefore, the present invention, which provides an increased anticoagulant activity of the Protein C anticoagulant pathway, provides for a high degree of resolution between different levels of Protein C activity and Protein S activity, provides a high degree of discrimination for the presence of the FV:$Q^{506}$ mutation, and results in an improved sensitivity and specificity for detection of defects in the Protein C anticoagulant pathway, through the use of metal ions in addition to calcium ions, could not be derived or expected from the prior art knowledge in the field.

A preferred embodiment of the present invention thus covers a method for the global screening for defects in the Protein C anticoagulant pathway of blood coagulation in a human, comprising (a) incubating a blood sample of said human comprising coagulation factors with:
  (1) an activator for the Protein C in the sample,
  (2) a suitable coagulation activator,
  (3) an exogenous synthetic substrate for either Factor Xa or thrombin comprising a photometrically measurable leaving group,
  (4) calcium ions, and
  (5) additional metal ions;
(b) determining the conversion rate of said exogenous substrate; and
(c) comparing said conversion rate with the conversion rate of a normal human blood sample determined in the same way.

A further preferred embodiment of the present invention relates to a method for the determination of free Protein S activity, comprising:

(a) incubating a human blood sample comprising coagulation factors with:
  (1) exogenous activated Protein C or exogenous Protein C together with an activator of Protein C,
  (2) a suitable coagulation activator,
  (3) an exogenous synthetic substrate for either Factor Xa or thrombin comprising a photometrically measurable leaving group,
  (4) calcium ions, and
  (5) additional metal ions;
(b) determining the conversion rate of said exogenous substrate; and
(c) comparing said conversion rate with the conversion rate of a normal human blood sample determined in the same way.

Another preferred embodiment of the present invention relates to a method for the determination of Protein C activity, comprising:

(a) incubating a human blood sample comprising coagulation factors with:
  (1) an activator for the Protein C in said sample,
  (2) a suitable coagulation activator,
  (3) an exogenous synthetic substrate for either Factor Xa or thrombin comprising a photometrically measurable leaving group,
  (4) calcium ions, and
  (5) additional metal ions;
(b) determining the conversion rate of said exogenous substrate; and
(c) comparing said conversion rate with the conversion rate of normal human blood sample determined in the same way.

A fourth preferred embodiment of the present invention is a method for screening for Factor V mutation(s) in a human blood sample, comprising:

(a) incubating a human blood sample comprising coagulation factors with:
  (1) exogenous activated Protein C, or exogenous Protein C together with an activator of Protein C, or an activator for endogenous Protein C,
  (2) a suitable coagulation activator,
  (3) an exogenous synthetic substrate for either Factor Xa or thrombin comprising a photometrically measurable leaving group,
  (4) calcium ions, and
  (5) additional metal ions;
(b) determining the conversion rate of said exogenous substrate; and
(c) comparing said conversion rate with the conversion rate of a normal human blood sample determined in the same way.

In the above preferred methods for global screening for defects in the Protein C anticoagulant pathway, for the determination of free Protein S activity or Protein C activity, or for screening for Factor V mutation(s) such as the FV:$Q^{506}$ mutation in a blood sample, step (a) comprises incubating the blood sample comprising coagulation factors in the presence of the additional metal ions used according to the present invention with (1) an activator for the Protein C in said sample to provide activation of endogenous Protein C, or exogenous activated Protein C or exogenous Protein C together with an activator of Protein C, (2) a suitable coagulation activator to provide at least partial activation of coagulation, (3) an exogenous synthetic substrate for either Factor Xa or thrombin comprising a photometrically measurable leaving group to provide for monitoring Factor $X_a$ or thrombin activity and (4) calcium ions to trigger coagulation.

These steps (1) to (4) can be performed simultaneously, separately and/or in different sequential combinations, providing for "one-step" to "four-step" methods as follows:

In a one-step method, all components necessary for performing steps (1) to (4) above are added simultaneously.

In two-step methods, (a) the components for steps (1) and (2) may first be combined followed by simultaneous addition of the exogenous substrate with calcium ions (3) and (4); or (b) all the components except the calcium ions may be added simultaneously, the addition of calcium ions then comprising the second step; or (c) the components for steps (1), (2) and (4) may be included simultaneously and step (3) be performed as a separate step.

In three-step methods, (a) steps (1) and (2) are combined and steps (3) and (4) are performed as separate steps; or (b) steps (1) and (2) are performed as separate steps and steps (3) and (4) are performed simultaneously; or (c) steps (2) and (3) are performed as separate steps, and steps (1) and (4) are performed simultaneously; or (d) step (1) is performed as a separate step, steps (2) and (4) are performed simultaneously, followed by step (3).

In four-step methods steps (1) to (4) are performed as separate steps in the order as described or in any other different order.

All one-, two-, three- or four-step methods may be used in chromogenic, fluorimetric and luminometric methods. Alternatively, in other embodiments of the invention, the methods may comprise measurements of clotting times, utilizing activation through the intrinsic, extrinsic or common pathways.

For any method, the additional metal ions used according to the present invention may be added either initially or at a later stage to any of the reagents. In applications where endogenous Protein C is activated by a Protein C activator, such as in methods for Protein C activity and global methods for the Protein C anticoagulant pathway, one preferred mode of the invention is to include the additional metal ions in the Protein C activation step, for example when Protac®C is used as the Protein C activator.

Specifically, the invention concerns the addition of divalent metal ions or of the monovalent copper ion, in order to increase the resolution between different levels of Protein C activity or Protein S activity, as well as to provide a high degree of discrimination for the presence of the FV:$Q^{506}$ mutation, resulting in an improved sensitivity and specificity for detection of defects in the Protein C anticoagulant pathway of blood coagulation. The range of concentrations of metal ions within which the anticoagulant activity of the Protein C system is stimulated varies with respect to the particular metal ion. The concentration range for metal ions other than $Mg^{2+}$ is preferably 1 $\mu$mol/L–2 mmol/L, more preferably 5–400 $\mu$mol/L, and most preferably 10–80 $\mu$mol/L. For $Mg^{2+}$ ions, the concentration range is preferably 20 $\mu$mol/L–10 mmol/L, more preferably 100 $\mu$mol/L–2 mmol/L, and most preferably 200 $\mu$mol/L–1 mmol/L.

The metal ions of the invention will typically be provided in combination with negatively charged counter ions. The counter ions should be selected to allow the metal ions to be available in solution at the above described concentrations. Suitable counter ions are mono-, di- and trivalent anions, preferably mono- and divalent anions, such as chloride, sulfate and nitrate anions. Alternatively, the metal ions could be provided in the form of metal ion complexes with proteins such as blood proteins, or on a solid surface such as a metal ion coated wall of a reaction vessel.

In preferred embodiments of the invention, photometric methods are used for monitoring the anticoagulant activity of components in the Protein C anticoagulant pathway. In such photometric methods, synthetic substrates with colorimetric, fluorimetric or luminometric leaving groups are used, which substrates preferably should be selective for Factor Xa or for thrombin. Because the generation of Factor Xa and thrombin is influenced by the Protein C anticoagulant activity in the reaction mixture, the measurement of the conversion rate of such substrates may be used for the determination of the activity of the Protein C anticoagulant pathway. The measurement of the conversion rate may be compared with the corresponding conversion rate obtained when using a normal human blood sample, or human pooled normal pool, as a test sample. The conversion rate may be measured kinetically (e.g., by monitoring the change in optical density (OD) versus time, expressed as e.g. ΔOD/min), or measured after a fixed incubation time, expressed as OD.

The determination of the conversion rate of synthetic substrates is performed with instruments suitable for monitoring the release of the leaving group from the particular substrate chosen. When the conversion rate is determined in a microplate reader, it is preferred to perform readings in the "dual wavelength mode" in order to eliminate possible differences between microplate wells. In this mode, one wavelength is selected for detecting the release of the leaving group, and another wavelength is selected in a range where the leaving group does not have any appreciable absorbance. When a calorimetric leaving group such as paranitroaniline (pNA) is chosen, a suitable dual wavelength reading may be performed at 405 and 490 nanometers, expressed as $OD_{405\text{-}490nm}$.

In preferred photometric methods, diluted blood samples are used in order to avoid interference of blood sample components in the test sample. The concentration of the blood sample in the final sample (i.e., the sample for which the optical density is determined) may vary depending on the actual method used. For example, for colorimetric methods the blood sample concentration may be below 10%, and is preferably below 5%.

The methods of the present invention allow for convenient reaction times such as 1–10 min, preferably 2–5 min, to provide for easy applicability to automated coagulation instruments.

A variety of activators of Protein C may be used in the methods of the present invention. For example, thrombin may be employed with or without thrombomodulin, and may be obtained from human or non-human sources, or may be produced by recombinant technology. Recombinantly produced protein may have either the wild-type protein sequence or a modified protein sequence which still provides suitable functional activity. Alternatively, a snake venom enzyme which activates Protein C may be employed. Suitable snake venom enzymes are preferably obtained from or derived from the Agkistrodon snake family, and may be added as crude venom, or in a purified preparation such as the product Protac®C. Suitable snake venom enzymes may also be produced by recombinant technology, having either the wild-type protein sequence or a modified protein sequence which still provides suitable functional activity. The concentration of the Protein C activator will vary depending on the particular assay conditions used. Thus, for the Protac®C activator, the concentration may vary between $1\times10^{-3}$ and 1 U/mL, preferably $2\times10^{-3}$ and 0.3 U/mL during the activation of Protein C in a global method for determining activity of the Protein C anticoagulant pathway, or in specific methods for determining Protein C and/or free Protein S activity, or for methods for detection of mutations in Factor V/Factor Va which affect the cleavage rate by APC.

In preferred embodiments of the present invention, the activation of Protein C in the blood sample precedes or occurs simultaneously with the activation of coagulation.

In preferred methods of the present invention, a suitable activator of coagulation is added to the assay medium or sample. Such activators may be selected to activate the intrinsic, extrinsic or common pathways of the coagulation cascade.

For example, activation through the intrinsic system may be accomplished with an APTT reagent containing a suitable contact activator, or with the separate addition of a contact activator. Suitable activators of the intrinsic pathway include compositions of phospholipids and contact activators. As contact activators, ellagic acid, collagen or collagen related substances, or various forms of silica (kaolin, micronized silica, colloidal silica) may be used. Alternatively, rather than using a contact activator, Factor XIIa, Factor XIa or Factor IXa may be used in combination with phospholipids as activators of the intrinsic pathway. Optionally, components such as prothrombin, Factor VIII/Factor VIIIa and Factor X may be added. Photometric substrates selective for Factor Xa or thrombin may also be used.

Activation through the extrinsic system may be accomplished by the addition of tissue factor, with or without the addition of Factor VII/Factor VIIa. The tissue factor may be obtained or derived from human or non-human sources, or may be produced by recombinant technology. Recombinantly produced protein may have either the wild-type protein sequence or a modified protein sequence which still provides suitable functional activity. Alternatively, activation may be accomplished by Factor VIIa in combination with phospholipids. Optionally, reagents such as prothrombin, Factor V/Va, Factor IX and Factor X may be added. Photometric substrates selective for FXa or thrombin may also be used.

Activation of the common pathway may be accomplished by addition of exogenous Factor Xa, or by addition of exogenous Factor X in combination with an exogenous activator of Factor X, such as a snake venom enzyme (e.g., snake venom enzyme from Russelli Viperii). Alternatively, the exogenous activator of Factor X may be added for activation of endogenous Factor X. Optionally, prothrombin and/or Factor V/Va may be added. Photometric substrates selective for thrombin may also be used.

In the above described modes for the activation or partial activation of coagulation according to the intrinsic, extrinsic or common pathways, phospholipids may be added as a mixture of synthetic phospholipids and/or purified phospholipids, or as crude extracts from biological sources such as brain, platelets, placenta, egg yolks or soybeans.

Generally, interference due to variable functional levels of components in the sample may be minimized by adding to the assay medium or sample a sufficient amount of plasma deficient in the Protein C anticoagulant pathway component to be measured. Thus, when measuring Protein C, Protein S, or Factor V activity, plasmas deficient in Protein C, Protein S or Factor V, respectively, may be employed. In the case of a global method for the Protein C anticoagulant pathway, a plasma deficient in each of Protein C, Protein S and Factor V may be added.

Thus, for example, in the case of a method for determining Protein S activity or a method for detection of a Factor V mutation which affects the degradation of Factor V/Va by APC, exogenous Protein C may be added in the form of a plasma deficient in Protein S or Factor V, respectively. Similarly, Protein S may be added in methods for Protein C activity or for the detection of mutations in Factor V. In the case of methods for determining Protein C and Protein S activity, Factor V/Factor Va may also be added to minimize interference from mutated Factor V which may be present in the sample.

The above-mentioned coagulation factors and components of the Protein C anticoagulant pathway, namely Factor XIIa, Factor XIa, Factor IX/IXa, Factor VIII/VIIIa, Factor VII/VIIa, Factor X/Xa, Factor V/Va, prothrombin, Protein C/APC and Protein S, may be of human or non-human origin, but are preferably of bovine or human origin. Said coagulation factors may also be produced by recombinant technology and have wild-type protein sequences or modified protein sequences which still provide suitable functional activity.

In preferred embodiments, in order to prevent fibrin gel formation, a fibrin polymerization inhibitor may be added to the reaction mixture, such as Gly-Pro-Arg-Pro or others known in the art.

In chromogenic methods, any chromogenic substrates for Factor Xa may be used, such as Benzoyl-Ile-Glu-Gly-Arg-pNA (S-2222, Chromogenix AB), N-a-Z-D-Arg-Gly-Arg-pNA (S-2765, Chromogenix AB), $CH_3SO_2$-D-Leu-Gly-Arg-pNA (CBS 31.39, Diagnostica Stago, Asnières, France) and MeO-CO-D-CHG-Gly-Arg-pNA (Spectrozyme Xa, American Diagnostica, Greenwich, USA). Correspondingly, any chromogenic substrates for thrombin may be used, such as H-D-Phe-Pip-Arg-pNA (S-2238, Chromogenix AB), pyroGlu-Pro-Arg-PNA (S-2366, Chromogenix AB), D-Ala-Pro-Arg-pNA (S-2846, Chromogenix AB), Z-D-Arg-Sarc-Arg-pNA (S-2796, Chromogenix AB), AcOH*H-D-CHG-But-Arg-pNA (CBS 34.47, Diagnostica Stago) and H-D-HHT-Ala-Arg-pNA (Spectrozyme TH, American Diagnostica).

In another aspect, the present invention provides kits for use in the above-described methods. In one preferred embodiment, a kit is provided comprising the following components:

(a) an activator for the endogenous Protein C in a sample, or exogenous activated Protein C, or exogenous Protein C together with an activator of Protein C;

(b) a suitable coagulation activator;

(c) an exogenous synthetic substrate for either Factor Xa or thrombin comprising a photometrically measurable leaving group;

(d) calcium ions; and (e) additional metal ions; in separate containers and/or in containers comprising mixtures of at least two of said components, and in aqueous solution or in lyophilized form.

In another preferred embodiment, a kit is provided comprising the following components:

(a) an activator for the endogenous Protein C in a sample, or exogenous activated Protein C, or exogenous Protein C together with an activator of Protein C;

(b) a suitable coagulation activator;

(c) an exogenous synthetic substrate for either Factor Xa or thrombin comprising a photometrically measurable leaving group;

(d) calcium ions;

(e) additional metal ions;

(f) coagulation factors; and in separate containers and/or in containers comprising mixtures of at least two of said components, and in aqueous solution or in lyophilized form.

In another aspect, the present invention provides a reagent for use in the above methods, and comprising said additional metal ions and at least one, and preferably at least two, of the following components (a) to (e):

(a) an activator for the endogenous Protein C in the sample, or exogenous activated Protein C, or exogenous Protein C together with an activator of Protein C;

(b) a suitable coagulation activator;

(c) an exogenous synthetic substrate for either Factor Xa or thrombin comprising a photometrically measurable leaving group;

(d) calcium ions; and (e) one or more coagulation factors; in one container in aqueous solution or in lyophilized form.

Thus, for example, in one preferred embodiment the reagent comprises activated Protein C, with or without calcium ions, as well as the additional metal ions. In another preferred embodiment, the reagent comprises coagulation factors and Protein C activators and, if desired, in combination with phospholipid(s), as well as the additional metal ions. In other embodiments, the reagent comprises Factor IX/IXa, Factor X/Xa and/or calcium ions, and the additional metal ions, or may comprise Factor V/Va, Protein C and prothrombin in combination with the additional metal ions. In another embodiment, Factor VIII/VIIIa and/or thrombin also may be combined with the additional metal ions. In yet another embodiment, the additional metal ions may be combined with a Protein C activator, such as Protac®C or thrombin/thrombomodulin. In all cases, the reagents may be suitably provided in a container, in aqueous solution or in lyophilized form.

A wide range of concentrations of reactants can be used in the methods of the present invention. Table 1 below presents suitable and preferred ranges for the various components used in the methods, and/or contained in the kits and reagents, as well as preferred ranges of pH and ionic strength. Naturally, higher concentrations may be contained in the kits, allowing for dilution before use.

TABLE 1

| Parameter | Final concentration in final reaction medium |
|---|---|
| Blood sample | 0.02–10%, preferably 0.1–5% (v/v) |
| FIX/FIXa | $1 \times 10^{-15}$–$1 \times 10^{-6}$ mol/L |
| FX/FXa | $1 \times 10^{-15}$–$5 \times 10^{-7}$ mol/L |
| FV/FVa | $1 \times 10^{-12}$–$10^{-7}$ mol/L, preferably $2 \times 10^{-10}$–$5 \times 10^{-8}$ mol/L |
| FVII/FVIIa | $1 \times 10^{-15}$–$2 \times 10^{-8}$ mol/L |
| FVIII/FVIIIa | $1 \times 10^{-4}$–$5 \times 10^{-1}$ IU/mL |
| Prothrombin | $1 \times 10^{-9}$–$5 \times 10^{-7}$ mol/L |
| Thrombin | $1 \times 10^{-15}$–$1 \times 10^{-8}$ mol/L |
| $Ca^{2+}$ ions | 0.5–20 mmol/L, preferably 1–10 mmol/L |
| $Mg^{2+}$ ions | 20 μmol/L–10 mmol/L, preferably 100 μmol/L–2 mmol/L, most preferably 200 μmol/L–1 mmol/L. |
| $Mn^{2+}$, $Zn^{2+}$, $Cu^{2+}$, $Ni^{2+}$, $Sr^{2+}$ and/or $Cu^{+}$ ions | 1 μmol/L–2 mmol/L, preferably 5–400 μmol/L, most preferably 10–80 μmol/L |
| Protein C/APC | $1 \times 10^{-10}$–$1 \times 10^{-7}$ mol/L, preferably $5 \times 10^{-10}$–$1 \times 10^{-8}$ mol/L |
| Protac ® C | $1 \times 10^{-3}$–1 U/mL, preferably $2 \times 10^{-3}$–0.3 U/mL |
| Protein S | $10^{-9}$–$5 \times 10^{-7}$ mol/L |
| Tissue factor | $10^{-8}$–$10^{-5}$ g/L, preferably $5 \times 10^{-8}$–$10^{-6}$ g/L |
| Thrombin/thrombomodulin | $10^{-11}$–$10^{-8}$ mol/L |
| Phospholipid | $1 \times 10^{-6}$–$3 \times 10^{-4}$ mol/L |
| Fibrin polymerization inhibitor | Range dependent on substance used |
| Chromogenic substrate | $10^{-5}$–$5 \times 10^{-3}$ mol/L |
| pH | 6.5–9.5, preferably 7–8.5 |
| Ionic strength | 0–0.6, preferably 0.01–0.25 |

Suitable embodiments include preparations of one or more of the components presented in Table 1, in aqueous solution or lyophilized in a container. For example, one or more of the proteins from Table 1 with and without additional metal ions, and optionally in the presence of phospholipid(s). Such embodiments may comprise, for example, Protein C or APC and said additional metal ions, optionally with calcium ions, and with or without an active enzyme such as Factor IXa or Factor Xa. Other embodiments may comprise the additional metal ions with one or more of Factor V/Va, Protein S, prothrombin, Factor X, Factor VIII/VIIIa, and thrombin. A further embodiment may comprise a Protein C activator such as Protac®C or thrombin/thrombomodulin with additional metal ions.

In particular, the present invention provides kits and reagents for use in the above-described in vitro methods for screening and diagnosing for Protein C and/or Protein S deficiency, and/or for mutations in Factor V which affect the anticoagulant activity of APC. More generally, the invention provides kits for in vitro methods for screening and diagnosing for defects in the Protein C pathway, including but not limited to those caused by Protein C deficiency, Protein S deficiency, and/or Factor V mutations.

EXAMPLES

Example 1

The effect of manganese and magnesium ions on the determination of Protein C activity in a three-stage, chromogenic, thrombin generation assay using the Protein C activator Protac®C was assessed as follows.

Samples: Protein C deficient plasma (Biopool AB, Umeå, Sweden) with and without addition of purified human Protein C (Chromogenix AB) to yield 0, 0.1, 0.5 and 1.0 IU/mL of Protein C.

Sample dilution: 1:41 in 25 mmol/L Tris-HCl, pH 7.6, 20 mmol/L NaCl, 0.2% bovine serum albumin.

Protein C activator: Protac®C was used as a stock solution containing 10 U/mL. Final concentration during activation of Protein C=0.17 U/mL. $Mg^{2+}$ and $Mn^{2+}$ ions were added to yield final concentrations during activation of Protein C of 0.4 and 0.04 mmol/L, respectively.

Reagent 1:

Bovine Factor IXa (Enzyme Research, South Bend, Ill.), 180 pmol/L

Bovine FX (Chromogenix AB), 0.3 U/mL

Reagent 2:

Phospholipids* (Chromogenix AB), 60 μmol/L

Gly-Pro-Arg-Pro, 0.36 mg/mL (polymerization inhibitor)

Human Factor V, 0.2 U/mL $CaCl_2$, 6 and 24 mmol/L (final conc. in assay=1.5 and 6 mmol/L)

* A mixture of purified phospholipids containing 43% phosphatidylcholine, 27% phosphatidylserine and 30% sphingomyelin.

Chromogenic thrombin substrate: S-2796 (Chromogenix AB), 2 mmol/L

Assay in a microplate: This assay is carried out as a three-stage method comprising, in the first stage, combining 50 μL of the diluted plasma with 50 μL of the Protein C activator and incubating this mixture for three minutes at 37° C., whereafter coagulation is activated by adding 50 μL of Reagent 1 and 50 μL of Reagent 2 and incubating the mixture for five minutes at 37° C., whereafter, in the third stage, the substrate hydrolysis is carried out by adding 50 μL of the chromogenic thrombin substrate S-2796 and incubating for four minutes at 37° C. The reaction is then terminated by lowering the pH through addition of 50 μL of 20% acetic acid. Thereafter the optical density (OD) of the samples in the microwells is recorded at 405 and 490 nm and the difference in optical density between 405 and 490 nm, $OD_{405\text{-}490nm}$, is calculated. This three-stage reaction is schematically shown as follows:

| | | |
|---|---|---|
| Protein C activation: | Plasma dilution | 50 μL |
| | Protein C activator | 50 μL |
| | 3 min, 37° C. | |
| Coagulation activation: | Reagent 1 | 50 μL |
| | Reagent 2 | 50 μL |
| | 5 min, 37° C. | |
| Substrate hydrolysis: | S-2796 | 50 μL |
| | 4 min, 37° C. | |
| | HOAc, 20% | 50 μL |
| Recording of $OD_{405\text{-}490\ nm}$ | | |

Results: The results are shown in the table below.

| | Protein C, IU/mL | | | |
|---|---|---|---|---|
| Ions | 0 | 0.1 | 0.5 | 1.0 |
| $Ca^{2+}$, 6 mmol/L | 0.542 | 0.515 | 0.503 | 0.467 |
| $Ca^{2+}$, 1.5 mmol/L + $Mn^{2+}$, 0.04 mmol/L | 0.564 | 0.441 | 0.231 | 0.076 |
| $Ca^{2+}$, 1.5 mmol/L + $Mg^{2+}$, 0.4 mmol/L | 0.541 | 0.441 | 0.230 | 0.069 |

The results demonstrate that by including manganese and magnesium ions in a reaction system containing calcium ions, a strong enhancement of the anticoagulant activity is obtained, manifested by the fact that increasing concentrations of Protein C in the samples result in a much decreased absorbance, i.e. a much decreased thrombin generation. In contrast, in the presence of calcium ions alone, there is a much lower resolution in absorbance, i.e. in thrombin generation, at increasing Protein C concentrations. Thus, the addition of the additional metal ions constitutes an improved method for determination of Protein C activity.

Example 2

The effect of different metal ions on the determination of Protein C activity in a three-stage thrombin generation assay using a four-fold lower concentration of Protein C activator was assessed.

Experimental conditions are as in Example 1, except for the use of a final concentration of the Protein C activator (Protac®C) of 0.043 U/mL. $Mg^{2+}$, $Mn^{2+}$, $Zn^{2+}$ and $Ni^{2+}$ ions were added to yield final concentrations during activation of Protein C of 0.4 mmol/L ($Mg^{2+}$) or 0.04 mmol/L. $Zn^{2+}$ ions, $Mn^{2+}$ ions and $Cu^{2+}$ ions were also added to yield a final concentration of 0.08 mmol/L. $Ca^{2+}$ was also used at final concentrations of 1.5 mmol/L and 6.6 mmol/L in the absence of other metal ions.

Results: The results are shown in the table below with all primary data, which also includes a comparison between final concentrations of 0.04 and 0.08 mmol/L for $Mn^{2+}$ and $Zn^{2+}$.

| | Protein C, IU/mL | | | |
|---|---|---|---|---|
| Ions | 0 | 0.1 | 0.5 | 1.0 |
| $Ca^{2+}$, 6 mmol/L | 0.652 | 0.633 | 0.559 | 0.505 |
| $Ca^{2+}$, 1.5 mmol/L | 0.640 | 0.585 | 0.504 | 0.438 |
| $Ca^{2+}$, 1.5 mmol/L + $Mn^{2+}$, 0.04 mmol/L | 0.725 | 0.689 | 0.503 | 0.237 |
| $Ca^{2+}$, 1.5 mmol/L + $Mn^{2+}$, 0.08 mmol/L | 0.627 | 0.469 | 0.145 | 0.056 |
| $Ca^{2+}$, 1.5 mmol/L+ $Mg^{2+}$, 0.4 mmol/L | 0.627 | 0.583 | 0.361 | 0.123 |
| $Ca^{2+}$, 1.5 mmol/L + $Zn^{2+}$, 0.04 mmol/L | 0.513 | 0.446 | 0.334 | 0.129 |
| $Ca^{2+}$, 1.5 mmol/L + $Zn^{2+}$, 0.08 mmol/L | 0.421 | — | 0.189 | 0.051 |
| $Ca^{2+}$, 1.5 mmol/L + $Ni^{2+}$, 0.04 mmol/L | 0.594 | 0.437 | 0.173 | 0.047 |
| $Ca^{2+}$, 1.5 mmol/L + $Cu^{2+}$, 0.08 mmol/L | 0.487 | 0.425 | 0.348 | 0.099 |

Figure 2:
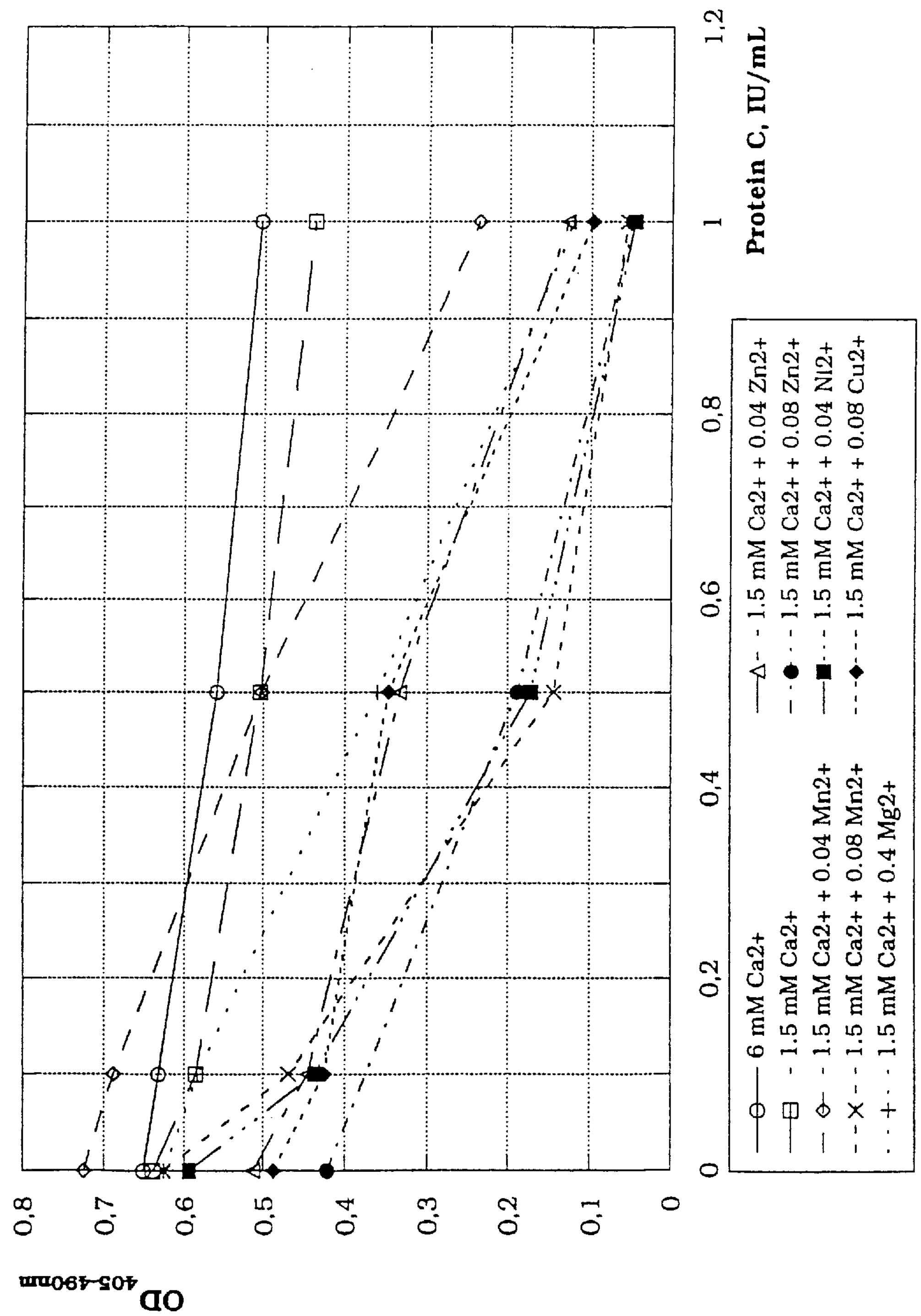
FIG. 2 is a graphic representation of the results obtained in Example 2, i.e., the effects of the metal ions in a chromogenic Protein C assay.

These results, which are graphically shown in FIG. 2, demonstrate that many different metal ions provide an enhancement of the anticoagulant activity, and also that a calcium concentration of 1.5 mmol/L in the absence of any other additional metal ions lacks the anticoagulation enhancement property. Furthermore, the concentration of Protac®C is not critical since the use of a four-fold lower concentration of this component still results in a pronounced anticoagulant activity in the presence of additional metal ions.

Example 3

The effect of metal ions on the determination of Protein C activity in a two-stage thrombin generation assay was assessed.

These experimental details are as described in Example 1, with the following exceptions:

(a) the final concentration of the Protein C activator (Protac®C) was 0.043 U/mL during activation of Protein C, (b) the chromogenic thrombin substrate used was S-2846 (Chromogenix AB), (c) the chromogenic substrate was included in Reagent 1, (d) purified human Protein C was added to Protein C deficiency plasma to yield 0, 0.1 and 0.5 IU/mL, and (e) the metal ions tested were $Mn^{2+}$ and $Mg^{2+}$.

Results: The results are shown in the table below expressed as $OD_{405\text{-}490nm}$:

| | Protein C, IU/mL | | |
|---|---|---|---|
| $Mn^{2+}$ ions | 0 | 0.1 | 0.5 |
| $Ca^{2+}$, 6 mmol/L | 1.18 | 1.07 | 0.669 |
| $Ca^{2+}$, 1.5 mmol/L+ $Mn^{2+}$, 0.04 mmol/L | 1.36 | 1.17 | 0.258 |
| $Ca^{2+}$, 6 mmol/L | 1.24 | 1.05 | 0.554 |
| $Ca^{2+}$, 1.5 mmol/L + $Mg^{2+}$, 0.4 mmol/L | 1.45 | 1.15 | 0.215 |

These results show that a significantly higher resolution for the different Protein C activities is obtained when $Mn^{2+}$ and $Mg^{2+}$ ions are added to a final concentration of 0.04 mmol/L and 0.4 mmol/L, respectively, thus constituting an improved two-stage method for determination of Protein C activity.

Example 4

The effect of manganese ions on the determination of Protein C activity in a two-stage thrombin generation assay using a phospholipid emulsion from bovine brain was assessed.

Phospholipid source: Cephotest (Nycomed, Oslo, Norway)

Experimental details are as in Example 3. The final concentration of Cephotest was 3% (v/v).

Results: The results are shown in the table below expressed as $OD_{405\text{-}490nm}$:

| | Protein C, IU/mL | | |
|---|---|---|---|
| Ions | 0 | 0.1 | 0.5 |
| $Ca^{2+}$, 6 mmol/L | 1.09 | 0.813 | 0.375 |
| $Ca^{2+}$, 1.5 mmol/L + $Mn^{2+}$, 0.04 mmol/L | 1.366 | 0.996 | 0.163 |

The results show that the same enhancing effect on the Protein C anticoagulant activity is obtained with a crude phospholipid extract from an animal tissue source. Hence, the source of phospholipid is not critical.

Example 5

The effect of manganese and magnesium ions on determination of free Protein S activity in a chromogenic Factor Xa generation assay was assessed.

Sample: Protein S deficient plasma (Biopool AB) with or without addition of purified human Protein S to yield 0%, 25% and 100% normal Protein S activity.

Sample dilution: 1:61 in 50 mmol/L Tris buffer pH 8.2, 0.15 mol/L NaCl, 0.2% BSA.

Factor reagent: (concentration in assay before substrate addition):

Bovine FIXa (4 mU/mL)

Bovine FX (0.3 U/mL)

Human FVIII (0.02 U/mL)

Human FV (0.02 U/mL)

Human prothrombin (0.01 U/mL)

Phospholipids (21 μmol/L)

$Mg^{2+}$ (0.4 mmol/L) or $Mn^{2+}$ (0.04 mmol/L) or no addition

Medium: 10 mmol/L MES pH 6.0, 0.15 mol/L NaCl, 0.2% BSA

Start reagent:

Human APC (0.35 μg/mL)

$CaCl_2$ (1.5 mmol/L)

Chromogenic Factor Xa substrate: S-2765 (Chromogenix AB), 1.8 mmol/L.

To carry out the assay, 50 μL of the diluted plasma sample was mixed with 50 μL of the above Factor reagent, whereafter the mixture was incubated for three minutes at 37° C. Thereafter, 50 μL of the Start reagent comprising human APC and calcium chloride was added and the mixture was incubated for four minutes at 37° C. Following that, 50 μL of the chromogenic substrate S-2765 was added and the reaction mixture incubated for two minutes at 37° C., whereafter 50 μL acetic acid was added to terminate the reaction. The absorbance of the sample was then determined according to Example 1 and expressed as $OD_{405\text{-}490nm}$.

| Assay: | | |
|---|---|---|
| | Factor reagent | 50 μL |
| | Sample dilution | 50 μL |
| | Incubation 3 min, 37° C. | |
| | $APC/CaCl_2$ | 50 μL |
| | 4 min, 37° C. | |
| | S-2765, 1.8 mmol/L | 50 μL |
| | 2 min, 37° C. | |
| | HOAc, 20% | 50 μL |

Results: All primary data are listed in the table below and also illustrated in FIG. 3.

| | Free Protein S, % | | |
|---|---|---|---|
| Ions | 0 | 25 | 100 |
| $Ca^{2+}$, 1.5 mmol/L | 0.857 | 0.642 | 0.364 |
| $Ca^{2+}$, 1.5 mmol/L + $Mn^{2+}$, 0.04 mmol/L | 1.53 | 1.34 | 0.745 |
| $Ca^{2+}$, 1.5 mmol/L + $Mg^{2+}$, 0.4 mmol/L | 1.053 | 0.851 | 0.378 |

Figure 3:
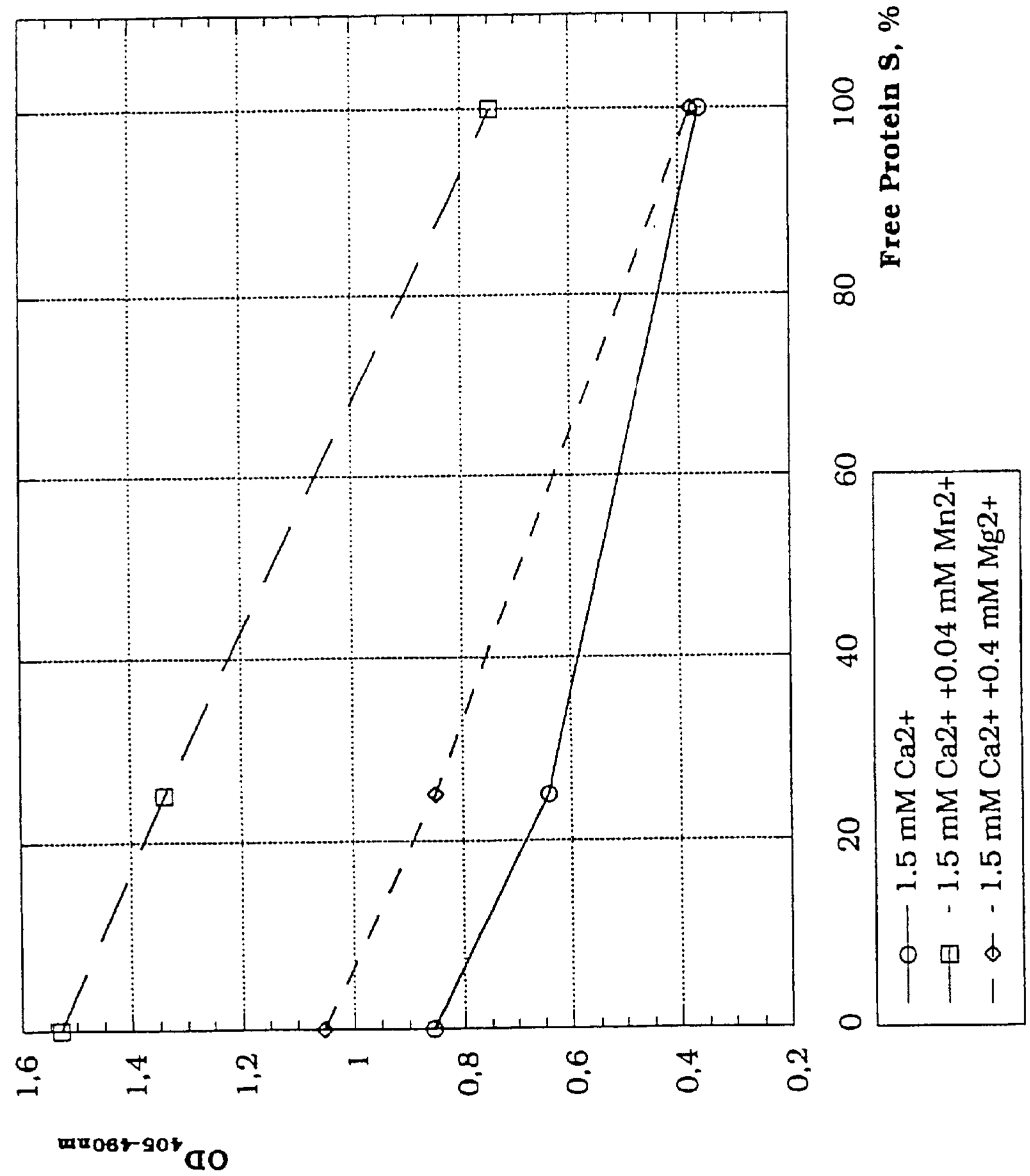
FIG. 3 is a graphic representation of the results obtained in Example 5, i.e., the effect of $Mg^{2+}$ and $Mn^{2+}$ in a chromogenic Protein S assay.

FIG. 3 shows that the addition of $Mg^{2+}$ or $Mn^{2+}$ ions results in a greater resolution (i.e., a greater slope of the curve), as well as in a more linear dose response when compared to the use of $Ca^{2+}$ alone, thus constituting an improved method for determination of Protein S activity.

Example 6

The effect of strontium ions on the determination of free Protein S activity in a chromogenic Factor Xa generation assay was assessed.

The experimental details are as disclosed in Example 5 but with the Factor reagent stored for one hour before assay.

Results: The results are shown in the table below expressed as $OD_{405\text{-}490nm}$:

| Ions | Free Protein S, % | | |
|---|---|---|---|
| | 0 | 25 | 100 |
| $Ca^{2+}$, 1.5 mmol/L | 0.673 | 0.488 | 0.258 |
| $Ca^{2+}$, 1.5 mmol/L + $Sr^{2+}$, 0.4 mmol/L | 0.848 | 0.611 | 0.276 |

The results show that a higher resolution for various Protein S activity levels is obtained on addition of $Sr^{2+}$ ions, supporting the enhancing effect of $Sr^{2+}$ on the Protein C anticoagulant pathway activity.

Example 7

The effect of metal ions on the detection of Protein S deficiency in a global chromogenic method for the Protein C anticoagulant pathway, using tissue factor as activator of coagulation and monitoring thrombin generation, was assessed.

Samples: Human pooled normal plasma and Protein S deficient plasma (Biopool AB).

Sample dilution: 1:21 in 25 mmol/L Tris-HCl, pH 7.6, 20 mmol/L NaCl, 0.2% bovine serum albumin.

Protein C activator: Protein C activator (Protac®C) from Coamatic Protein C kit (Chromogenix AB) was reconstituted in 7.2 mL according to the package insert and then diluted in 25 mmol/L Tris-HCl, pH 7.6, 20 mmol/L NaCl, 0.2% bovine serum albumin to yield a concentration during Protein C activation of 0.02 U/mL. Human prothrombin (Chromogenix AB) was added to yield a final concentration after addition of tissue factor of 1.5 μg/mL.

The analysis was performed with or without $Mg^{2+}$ ions added to the Protac®C solution.

Tissue factor: Thromborel (Behringwerke, Marburg, Germany). Reconstituted in 2 mL water according to the manufacturer's instructions, thereafter diluted in 25 mmol/L Tris-HCl, pH 7.6, 20 mmol/L NaCl, 0.2% bovine serum albumin to yield a final concentration during activation of coagulation of 0.033% (v/v).

Phospholipids: 43% phosphatidylcholine, 27% phosphatidylserine and 30% sphingomyelin (Chromogenix AB). Final concentration during activation of coagulation of 16.7 μmol/L.

$CaCl_2$: 6.6 mmol/L final concentration during activation of coagulation.

Chromogenic thrombin substrate: S-2796 (Chromogenix AB), 1.8 mmol/L.

To carry out the assay, 50 μL of the diluted plasma sample was mixed with 50 μL of the Protein C activator, whereafter the mixture was incubated for two minutes at 37° C. Thereafter, 50 μL of the reagent comprising the tissue factor was added and the mixture was incubated for two minutes at 37° C. Following that, 50 μL of the chromogenic substrate S-2796 was added and the reaction mixture incubated for four minutes at 37° C., whereafter 50 μL acetic acid solution was added to terminate the reaction. The absorbance of the sample was then determined according to Example 1 and expressed as $OD_{405\text{-}490nm}$.

| Microplate Assay: | |
|---|---|
| Sample dilution | 50 μL |
| Protac C activator | 50 μL |
| 2 min, 37° C. | |
| Reagent | 50 μL |
| 2 min, 37° C. | |
| S-2796 | 50 μL |
| 4 min, 37° C. | |
| HOAc, 20% | 50 μL |

Results: The results are shown in the table below.

| Ions | Normal plasma | Protein S def. plasma |
|---|---|---|
| $Ca^{2+}$, 6.6 mmol/L | 0.26 | 0.53 |
| $Ca^{2+}$, 6.6 mmol/L + $Mg^{2+}$, 0.4 mmol/L | 0.29 | 0.75 |

The results show that the addition of magnesium ions to calcium ions brings about a higher resolution at different Protein S activity levels, thus improving detection of Protein S deficiency.

Example 8

The effect of metal ions on the resolution between different levels of free Protein S, and for detection of FV:$Q^{506}$, in a global method for the Protein C anticoagulant pathway, using Factor Xa as activator of coagulation and monitoring thrombin generation, was assessed.

Experimental details are as in Example 7, but with bovine Factor Xa (Chromogenix AB) used instead of tissue factor as activator of coagulation. Concentration of Factor Xa=1.4 ng/mL during activation. Furthermore, a stock solution of Protac®C, containing 10 U/mL, was used, which was then diluted in 25 mmol/L Tris-HCl, pH 8.4, 0.2% bovine serum albumin to yield a concentration during protein C activation of 0.02 U/mL.

| Samples: | | |
|---|---|---|
| | 100% protein S = | human pooled normal plasma |
| | 0% protein S = | protein S deficient plasma |
| | 25% protein S = | protein S deficient plasma + 2.5 μg/mL purified human protein S. |

Furthermore, a sample from an individual with heterozygosity for the factor V mutation (FV:R506Q) was analyzed.

Figure 4:
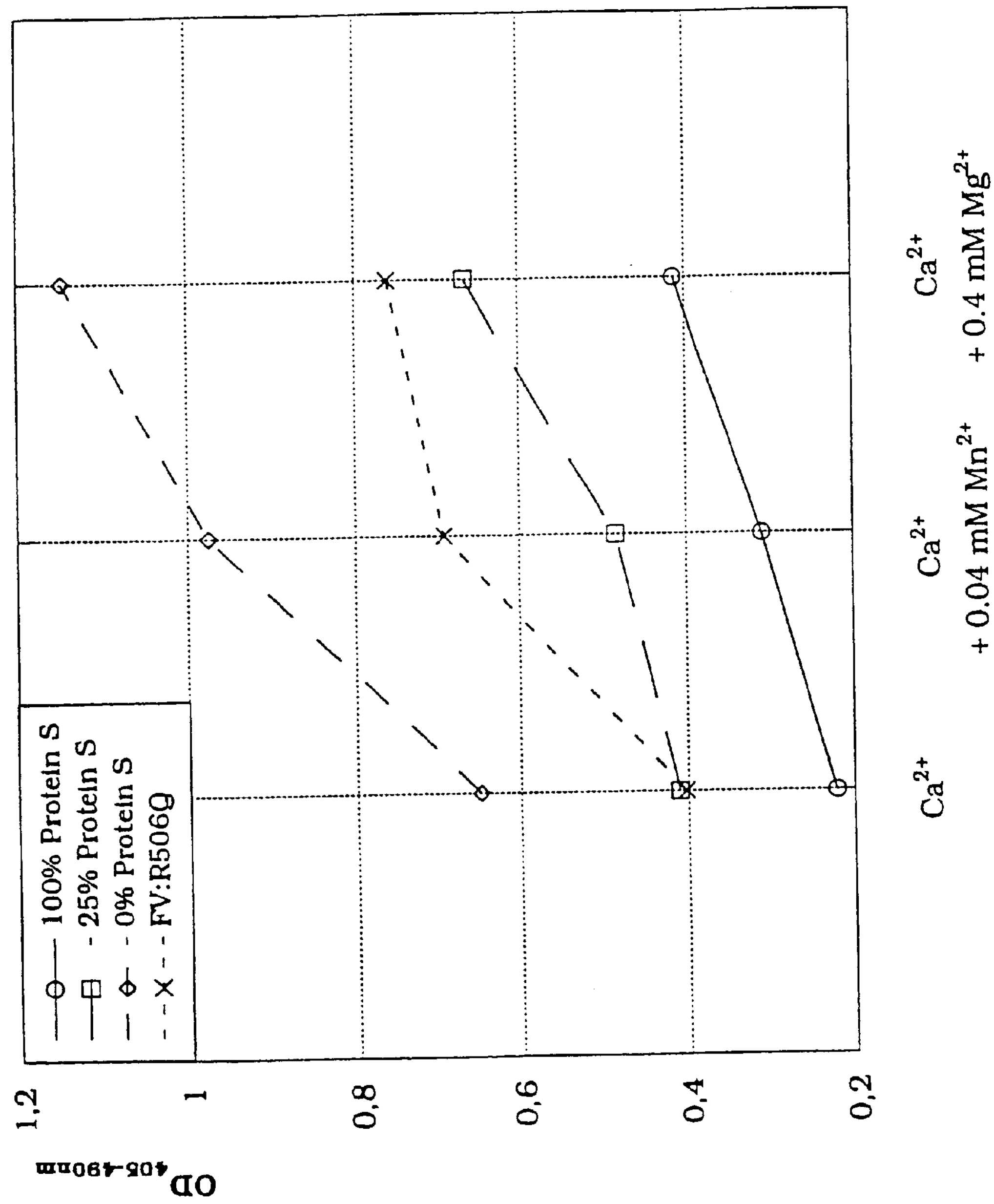
FIG. 4 is a graphic representation the results obtained in Example 8, i.e., the effect of metal ions on discrimination for Protein S deficiency and for FV:$Q^{506}$ in a global Protein C pathway assay using Factor Xa as activator.

Results: See FIG. 4. The table below presents all primary data expressed as $OD_{405\text{-}490nm}$.

| Sample | Only $Ca^{2+}$ | $Ca^{2+}$ + 0.04 mM $Mn^{2+}$ | $Ca^{2+}$ + 0.4 mM $Mg^{2+}$ |
|---|---|---|---|
| 100% Protein S | 0.222 | 0.309 | 0.144 |
| 25% Protein S | 0.411 | 0.485 | 0.667 |
| 0% Protein S | 0.650 | 0.975 | 1.147 |
| FV:R506Q | 0.402 | 0.693 | 0.761 |

The results show that a higher resolution is obtained for Protein S deficiency in the 0–100% range as well as a high discrimination for the FV:$Q^{506}$ mutation when $Mg^{2+}$ or $Mn^{2+}$ ions are included in the reaction mixture, thus proving the beneficial use of added metal ions in a global chromogenic method.

Example 9

A comparison was made between a global chromogenic method according to the invention, using Factor Xa as coagulation activator, with a global clotting method according to the prior art, using an APTT reagent as coagulation activator, regarding the resolution between different levels of Protein C and Protein S activity, and regarding the analysis of plasma from pregnant women.

Samples: Human pooled normal plasma (PNP), three plasmas from healthy individuals (N1–N3), and four plasmas from pregnant women (P1–P4) were tested. In addition, plasmas with 0% and 50% deficiency of Protein C (0% Pr C and 50% PrC, respectively), and plasmas with 0% and 50% deficiency of Protein S (0% Pr S and 50% Pr S, respectively), were tested. The 50% Pr C and PR S plasmas were prepared by adding purified human Protein C (Chromogenix AB) or Protein S (Chromogenix AB) to plasmas deficient in either Protein C or S (both from Biopool AB).

Global chromogenic assay: Experimental details and assay are as in Examples 7 and 8. A stock solution of Protac®C, initially containing 10 U/mL, was diluted to yield a final concentration during activation of Protein C=0.02 U/mL. The additional metal ion employed was $Mn^{2+}$, which was added to the Protac®C solution to yield 0.04 mmol/L in the Protein C activation step. The analysis was performed in a microplate, and the $OD_{405-490}$ was determined as described in Example 1. A high $OD_{405-490}$ corresponds to pronounced thrombin formation and thus an impaired Protein C anticoagulant pathway activity.

Global clotting assay using APTT reagent: APTT reagent from Coatest® APC Resistance kit (Chromogenix AB) was used at a final phospholipid concentration of 33 μmol/L during coagulation activation. For activation of Protein C, the same Protac®C stock solution and dilution medium was used as for the chromogenic assay. The final concentration during activation of Protein C was 0.083 U/mL. The analysis was performed in a ST-4 coagulation analyzer (Diagnostica Stago).

| Assay: | |
|---|---|
| Plasma sample | 50 μL |
| Protac ® C or buffer | 50 μL |
| APTT reagent | 50 μL |
| Activation for 3 min, 37° C. | |
| $Ca^{2+}$, 25 mmol/L | 50 μL |

The clotting time in seconds was determined in the presence (CT+) and absence (CT−) of Protac®C and a clot time ratio (CTR) was calculated as CTR=CT+/CT−. A low CTR corresponds to pronounced thrombin formation even in the presence of Protac®C, and hence an impaired Protein C anticoagulant pathway activity.

Results: The results are shown in the table below.

| Sample | Chromogenic $OD_{405-490}$ | APTT CTR |
|---|---|---|
| PNP | 0.202 | 3.77 |
| N1 | 0.183 | 5.17 |
| N2 | 0.182 | 3.50 |
| N3 | 0.186 | 4.85 |
| P1 | 0.221 | 3.15 |
| P2 | 0.298 | 2.21 |
| P3 | 0.239 | 2.60 |
| P4 | 0.259 | 2.66 |
| 50% Pr S | 0.578 | 3.48 |
| 0% Pr S | 0.802 | 1.80 |
| 50% Pr C | 0.456 | 3.86 |
| 0% Pr C | 1.084 | 1.18 |

The results demonstrate that (a) for samples with 50% deficiency of either Protein C or Protein S, a higher resolution was obtained versus the normal samples and (b) for samples from pregnant women, a smaller deviation from normal samples is obtained with the chromogenic assay, thus supporting the conclusion that a higher sensitivity and specificity will be obtained with a global chromogenic assay according to the invention as compared to a global clotting method according to the prior art.

Example 10

The effect of a mixture of $Mg^{2+}$ and $Mn^{2+}$ in a phospholipid reagent or in an APC reagent on the discrimination of the FV:$Q^{506}$ mutation in a chromogenic thrombin generation assay, using Factor Xa as activator, was assessed.

Sample: Plasmas with normal Factor V (R506R), and with heterozygosity (R506Q) and homozygosity (Q506Q) for FV:$Q^{506}$ mutation.

Sample dilution: 1:41 in 0.05 mol/L HEPES, pH 7.7, 0.15 mol/L NaCl.

Reagent A:

Human prothrombin, 19 μg/mL

Phospholipids (43% phosphatidylcholine, 27% phosphatidylserine and 30% sphingomyelin), 50 μmol/L Reagent B:

Bovine Factor Xa, 0.2 nmol/L

APC, 6 μg/mL $CaCl_2$, 25 mmol/L

Chromogenic thrombin substrate: S-2796 (Chromogenix AB), 1.8 mmol/L

Mixture of metal ions: $Mg^{2+}$, 0.4 mmol/L, and $Mn^{2+}$, 0.04 mmol/L, included in either Reagent A or Reagent B.

To carry out the assay, 50 μL of Reagent A was mixed with 50 μL of Reagent B, whereafter the mixture was incubated for three minutes at 37° C. Thereafter, 50 μL of the plasma dilution was added and incubated for two minutes at 37° C. Following that, 50 μL of the chromogenic substrate S-2796 was added and kinetic analysis was performed. The change in $OD_{405-490}$ per minute was determined and expressed as $\Delta OD_{405-490}$/min.

| Assay: | |
|---|---|
| Reagent A | 50 μL |
| Reagent B | 50 μL |
| Incubate at 37° C. for 3 min | |
| Plasma dilution | 50 μL |
| 2 min, 37° C. | |
| S-2796 | 50 μL |
| Kinetic reading | |

Results: The results are shown in the table below.

| | $Mg^{2+}$ and $Mn^{2+}$ in Reagent A | $Mg^{2+}$ and $Mn^{2+}$ in Reagent B |
|---|---|---|
| FV:R506R | 0.143 | 0.193 |
| FV:R506Q | 0.646 | 0.616 |
| FV:Q506Q | 1.116 | 0.942 |

The results show that a mixture of metal ions, such as $Mg^{2+}$ and $Mn^{2+}$, may be added in a phospholipid containing reagent (Reagent A), or in a reagent containing active enzymes such as APC and Factor Xa (Reagent B), and can provide a high discrimination for the FV:$Q^{506}$ mutation. Hence the addition of additional metal ions is not restricted to any unique reagent.

Example 11

The substitution of chloride anions with nitrate and sulfate anions was assessed in a study on the effect of magnesium and manganese in determination of Protein C activity in a three-stage thrombin generation assay.

Experimental details are as in Example 1, except that magnesium nitrate ($Mg(NO_3)_2$) and manganese sulfate ($MnSO_4$) were used instead of the corresponding chloride salts at final concentrations in the assay of 0.4 and 0.04 mmol/L, respectively, in accordance with the conditions in Example 1.

Results: The results are shown in the table below expressed as $OD_{405\text{-}490nm}$.

| | Protein C, IU/mL | | | |
|---|---|---|---|---|
| Ions | 0 | 0.1 | 0.5 | 1.0 |
| $Ca^{2+}$, 1.5 mmol/L + $Mn^{2+}$, 0.04 mmol/L | 0.563 | 0.541 | 0.278 | 0.079 |
| $Ca^{2+}$, 1.5 mmol/L + $Mg^{2+}$, 0.4 mmol/L | 0.603 | 0.554 | 0.448 | 0.154 |

The results show that a similar high resolution is obtained as when using chloride as an anion (cf. Example 1). Thus, the choice of the anion is not restricted to chloride ions.

Example 12

The effect of metal ions on the detection of Protein C deficiency, Protein S deficiency, and the FV:$Q^{506}$ mutation was assessed in a global chromogenic method for the Protein C anticoagulant pathway, using recombinant tissue factor as activator of coagulation and monitoring thrombin generation.

Experimental details are as in Example 7, but using recombinant tissue factor (PT-Fibrinogen Recombinant, Instrumentation Laboratory, Milano, Italy) instead of Thromborel as activator of coagulation. PT-Fibrinogen Recombinant was reconstituted with 8 mL of water according to the manufacturer's instructions, thereafter diluted in 25 mmol/L Tris-HCl, pH 7.6, 20 mmol/L NaCl, 0.2% bovine serum albumin to yield a final concentration during activation of coagulation of 0.25% (v/v).

Samples: Normal human plasma, Protein C deficient plasma, and Protein S deficient plasma (Instrumentation Laboratory, Milano, Italy). Plasmas with 25% activity of Protein C and Protein S, respectively, were prepared by mixing normal human plasma with the Protein C or Protein S deficient plasmas respectively. Furthermore, a sample from an individual with heterozygosity for the factor V mutation (FV:R506Q) and from an individual with homozygosity for the same mutation (FV:Q506Q) were analyzed.

The analysis was performed with or without $Mg^{2+}$ ions added to the Protein C activator solution.

Figure 5:
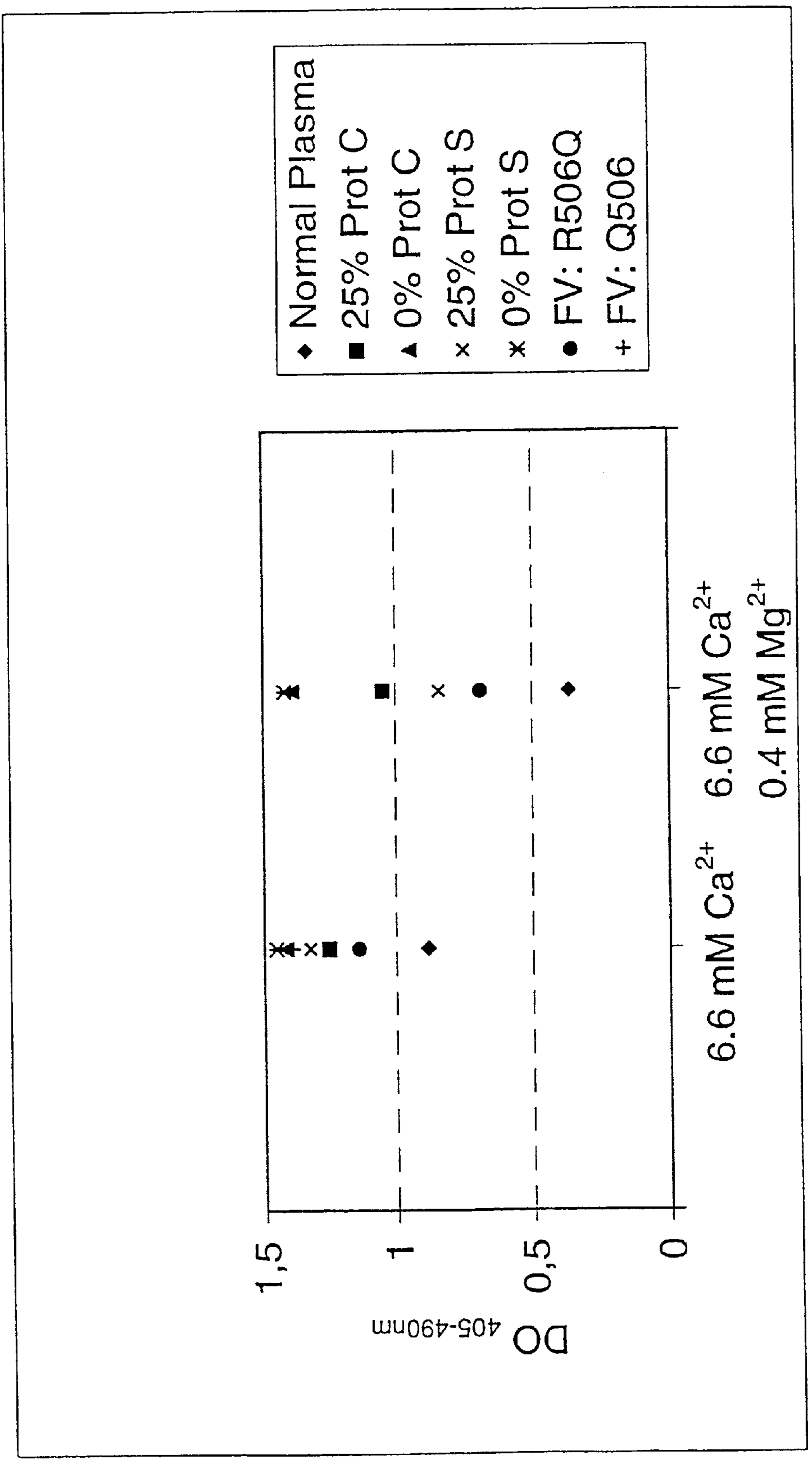
FIG. 5 is a graphic representation of the results obtained in Example 12, i.e., the effect of $Mg^{2+}$ in a global chromogenic assay for the detection of Protein C deficiency, Protein S deficiency, and the FV:$Q^{506}$ mutation using a recombinant tissue factor.

Results: See FIG. 5. The table below presents all primary data expressed as $OD_{405\text{-}490nm}$.

| Sample | 6.6 mM $Ca^{2+}$ | 6.6 mM $Ca^{2+}$ + 0.4 mM $Mg^{2+}$ |
|---|---|---|
| Normal Plasma | 0.881 | 0.364 |
| 25% Protein C | 1.225 | 1.047 |
| 0% Protein C | 1.418 | 1.388 |
| 25% Protein S | 1.325 | 0.837 |
| 0% Protein S | 1.456 | 1.421 |
| FV:R506Q | 1.140 | 0.686 |
| FV:Q506Q | 1.392 | 1.398 |

The results show that the presence of magnesium ions during the Protein C activation and during the ensuing thrombin generation provides an enhancement of the anticoagulant activity (see results for normal plasma). Furthermore, the enhanced anticoagulant activity results in a higher resolution at different Protein C and Protein S activity levels, as well as higher discrimination for the FV:$Q^{506}$ mutation.

Example 13

The effect of manganese ions on the discrimination at different Protein S activity levels was assessed in a global chromogenic method for the Protein C anticoagulant pathway, using tissue factor as activator of coagulation and monitoring thrombin generation.

Experimental details are as in Example 7, using Protac®C as the Protein C activator and Thromborel as activator of coagulation.

Samples: Normal human plasma (Instrumentation Laboratory, Milano, Italy) was used as the 100% Protein S sample; and Protein S deficient plasma (Instrumentation Laboratory, Milano, Italy) was used as the 0% Protein S sample. Additional plasma samples were prepared by mixing normal human plasma and Protein S deficient plasma to yield plasmas with 20%, 40%, 60% and 80% Protein S activity respectively.

The analysis was performed with or without $Mn^{2+}$ ions added to the Protein C activator solution.

Results: All primary data expressed as $OD_{405\text{-}490nm}$ are listed in the table below and are also illustrated in FIG. 6.

| Sample | 6.6 mM $Ca^{2+}$ | 6.6 mM $Ca^{2+}$ + 0.04 mM $Mn^{2+}$ |
|---|---|---|
| 0% Protein S | 0.458 | 1.371 |
| 20% Protein S | 0.407 | 0.756 |
| 40% Protein S | 0.388 | 0.570 |
| 60% Protein S | 0.367 | 0.493 |
| 80% Protein S | 0.348 | 0.439 |
| 100% Protein S | 0.325 | 0.379 |

Figure 6:
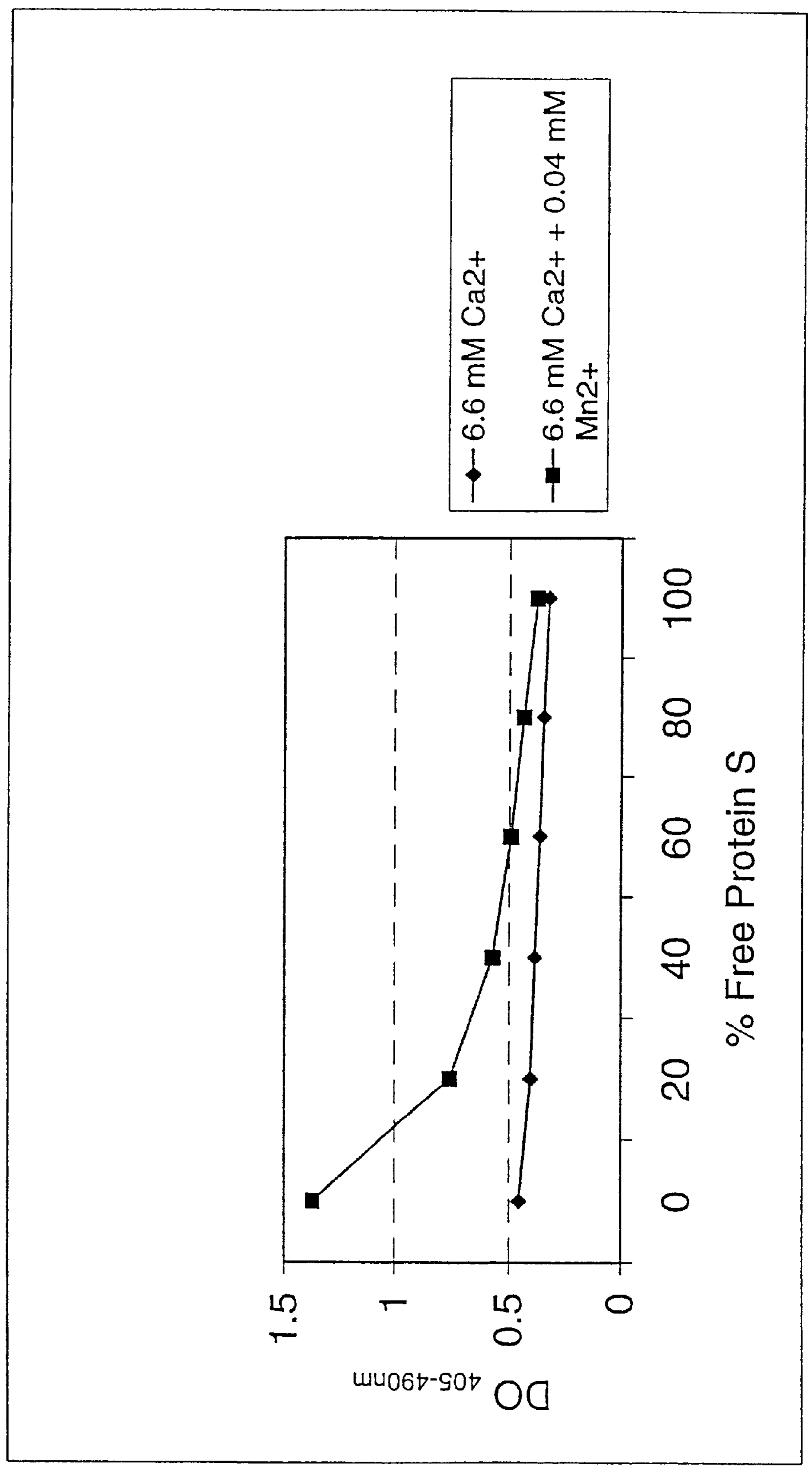
FIG. 6 is a graphic representation of the results obtained in Example 13, i.e., the effect of $Mn^{2+}$ on the determination of free Protein S activity in a chromogenic thrombin generation assay.

FIG. 6 shows that the addition of $Mn^{2+}$ ions dramatically increases the resolution when compared to the use of $Ca^{2+}$ alone, thus constituting an improved detection of Protein S deficiency in a global chromogenic method for detection of deficiency states of components in the Protein C anticoagulant pathway.

Example 14

The effect of magnesium and manganese ions on the discrimination at different Protein C activity levels was assessed in a global chromogenic method for the Protein C anticoagulant pathway, using recombinant tissue factor as the activator of coagulation, a recombinant Protein C activator, and monitoring thrombin generation.

Experimental details are as in Example 7, but using recombinant Protein C activator as Protein C activator and recombinant tissue factor (PT-Fibrinogen Recombinant, Instrumentation Laboratory) as activator of coagulation. Recombinant Protein C activator was used as a stock solution containing 26 U/mL. The recombinant Protein C activator was then diluted in 25 mmol/L Tris-HCl, pH 7.6, 20 mmol/L NaCl, 0.2% bovine serum albumin to yield a final concentration during activation of Protein C of 0.025 U/mL. PT-Fibrinogen Recombinant was prepared as in Example 12 to yield a concentration during activation of coagulation of 0.17% (v/v).

Samples: Normal human plasma (Instrumentation Laboratory, Milano, Italy) was used as the 100% Protein C sample; Protein C deficient plasma (Instrumentation Laboratory, Milano, Italy) was used as the 0% Protein C sample; and additional plasma samples were prepared by mixing normal human plasma and Protein C deficient plasma to yield plasmas with 20%, 40%, 60% and 80% Protein C activity respectively.

The analysis was performed with or without $Mg^{2+}$ or $Mn^{2+}$ ions added to the recombinant Protein C activator solution.

Results: All primary data expressed as $OD_{405\text{-}490nm}$ are listed in the table below and also illustrated in FIG. 7.

| Sample | 6.6 mM $Ca^{2+}$ | 6.6 mM $Ca^{2+}$ + 0.4 mM $Mg^{2+}$ | 6.6 mM $Ca^{2+}$ + 0.4 mM $Mn^{2+}$ |
|---|---|---|---|
| 0% Protein C | 1.442 | 1.483 | 1.451 |
| 20% Protein C | 1.253 | 1.219 | 1.097 |
| 40% Protein C | 1.010 | 0.900 | 0.636 |
| 60% Protein C | 0.783 | 0.675 | 0.438 |
| 80% Protein C | 0.787 | 0.569 | 0.356 |
| 100% Protein C | 0.672 | 0.456 | 0.280 |

Figure 7:
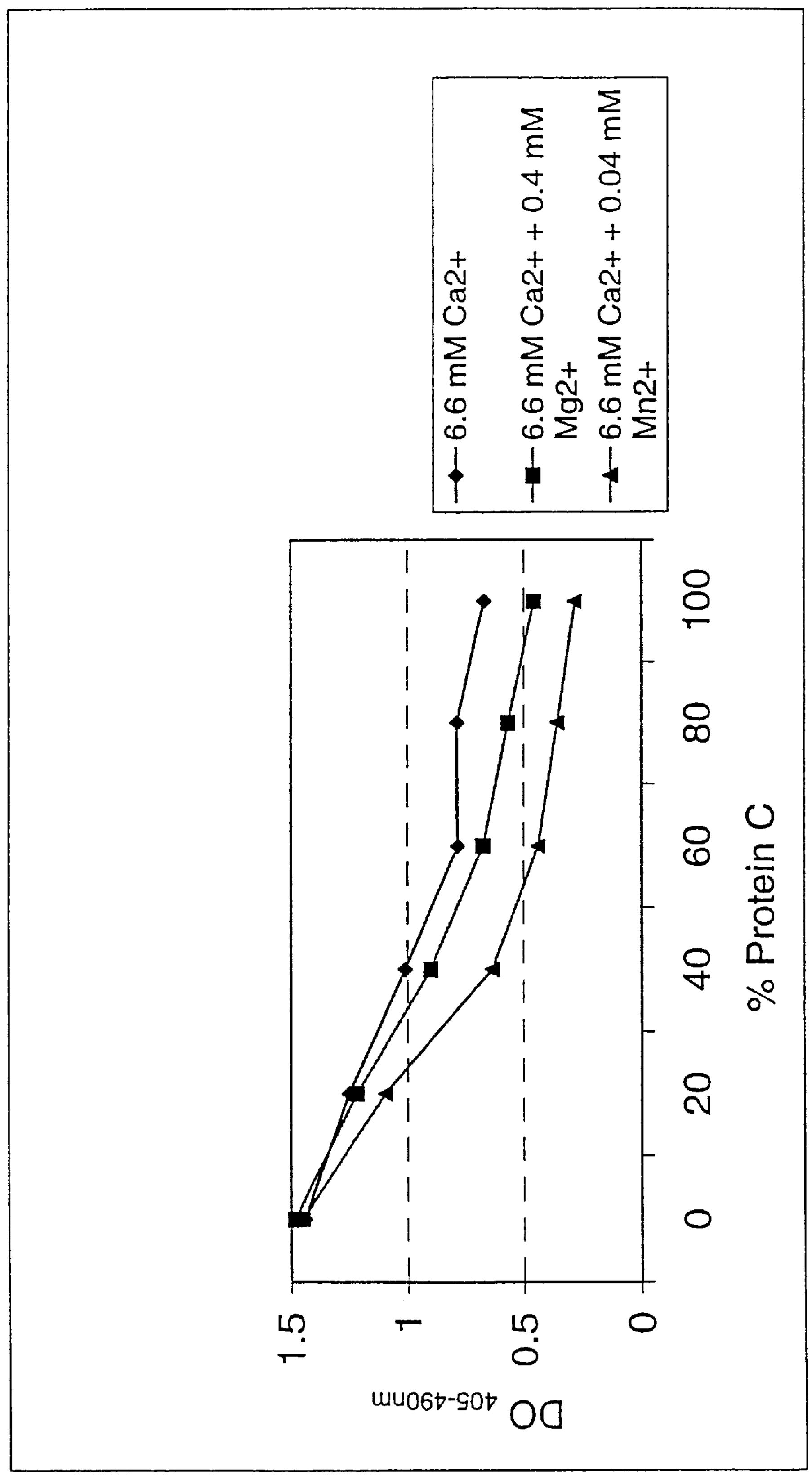
FIG. 7 is a graphic representation of the results obtained in Example 14, i.e., the effect of $Mg^{2+}$ and $Mn^{2+}$ on the determination of Protein C activity in a chromogenic thrombin generation assay.

FIG. 7 shows that the addition of $Mg^{2+}$ or $Mn^{2+}$ ions results in a higher resolution for the different Protein C activities when compared to the use of $Ca^{2+}$ alone, thus resulting in an improved detection of Protein C deficiency in a global chromogenic method for detection of deficiency states of components in the Protein C anticoagulant pathway.

Example 15

The effect of the combination of $Mg^{2+}$ and $Mn^{2+}$ ions on the detection of Protein C deficiency, Protein S deficiency and the FV:$Q^{506}$ mutation was assessed in a global chromogenic method for the Protein C anticoagulant pathway, using tissue factor as activator of coagulation and monitoring thrombin generation.

Experimental details are as in Example 7, using Protac®C as the Protein C activator and Thromborel as the activator of coagulation.

Samples: Normal human plasma, Protein C deficient plasma and Protein S deficient plasma (Instrumentation Laboratory, Milano, Italy). Furthermore, a sample from an individual heterozygous for the Factor V mutation (FV:R506Q) and from an individual homozygous for the same mutation (FV:Q506Q) were analyzed.

The analysis was performed with or without the presence of the combination of $Mg^{2+}$ and $Mn^{2+}$ ions added to the Protein C activator solution.

Figure 8:
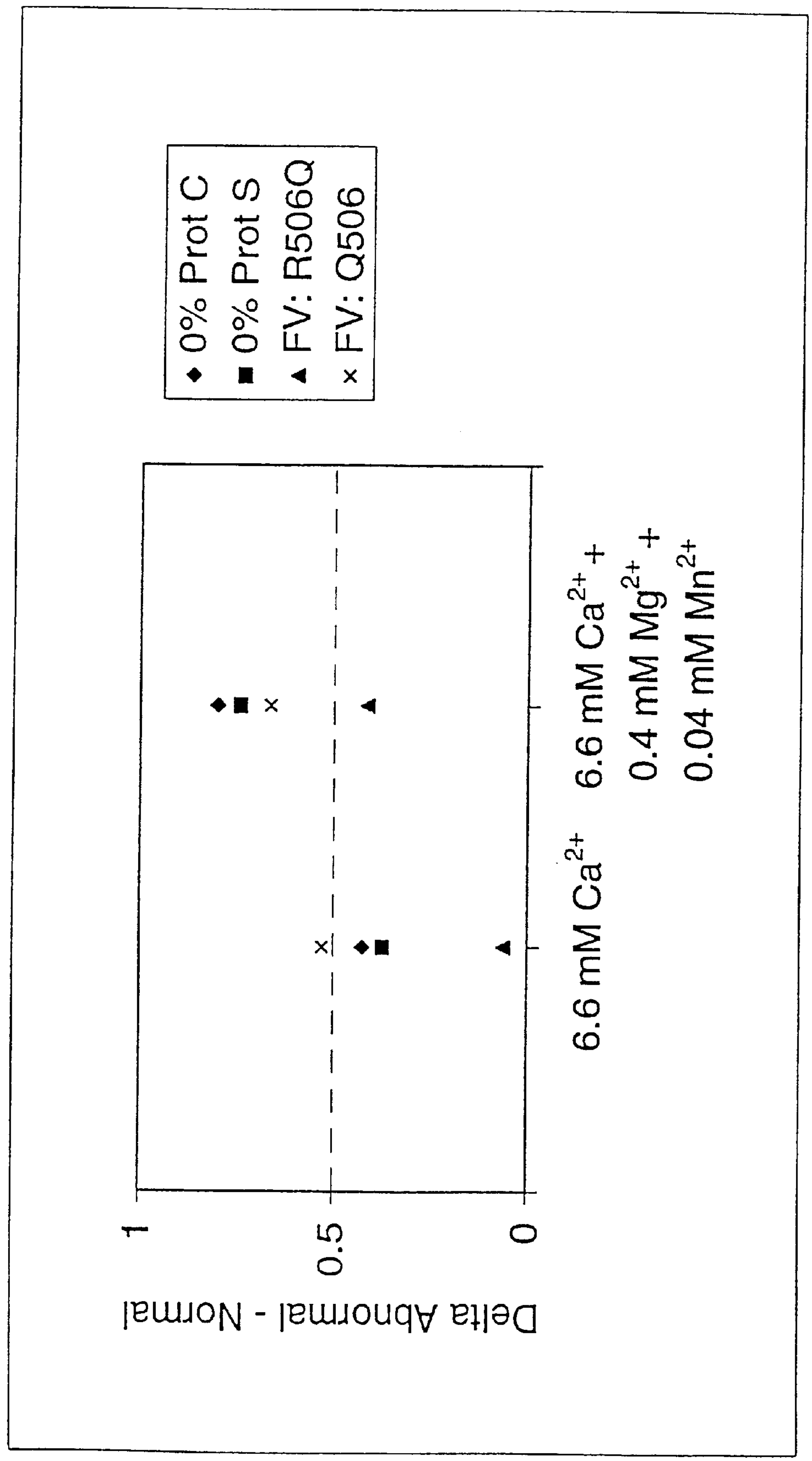
FIG. 8 is a graphic representation of the results obtained in Example 15, i.e., the effect of $Mg^{2+}$ and $Mn^{2+}$ on the detection of Protein C deficiency, Protein S deficiency and the FV:$Q^{506}$ mutation in a global chromogenic method using a recombinant tissue factor as activator of coagulation and monitoring thrombin generation.

Results: See FIG. 8. The table below presents all primary data expressed as Δ Abnormal−Normal (i.e., $OD_{405\text{-}490}$ abnormal plasma−$OD_{405\text{-}490}$ normal plasma).

| Sample | 6.6 mM Ca2+ | 6.6 mM Ca2+ + 0.4 mM Mg2+ + 0.04 mM Mn2+ |
|---|---|---|
| 0% Protein C | 0.425 | 0.801 |
| 0% Protein S | 0.372 | 0.742 |
| FV:R506Q | 0.060 | 0.413 |
| FV:Q506Q | 0.530 | 0.664 |

The results show that the addition of the combination of magnesium and manganese ions to calcium ions provide a higher resolution for both Protein C and Protein S deficiencies, as well as a higher discrimination for the FV:$Q^{506}$ mutation, thus proving the beneficial use of adding a combination of metal ions in a global chromogenic method.

What is claimed is:

1. An in vitro method for qualitative screening and quantitative determination of the functional activity of one or more components of the Protein C anticoagulant pathway of the blood coagulation system, comprising:

(a) providing a blood sample to be analyzed;

(b) activating the coagulation cascade by adding a procoagulant reagent to the blood sample to be analyzed, wherein the procoagulant reagent activates coagulation via a pathway selected from the group consisting of the intrinsic pathway, the extrinsic pathway, and the common pathway;

(c) triggering coagulation by adding calcium ions to the blood sample;

(d) adding metal ions selected from the group consisting of $Mn^{+2}$, $Zn^{+2}$, $Ni^{+2}$, $Sr^{+2}$, $Cu^{+2}$, or $Cu^{+}$ ions at a concentration that increases the anticoagulant activity of the Protein C anticoagulant pathway;

(e) adding an exogenous substrate for an enzyme influenced by Protein C anticoagulant activity;

(f) incubating a reaction mixture comprising the components recited in steps (a)–(e);

(g) measuring the conversion rate of the exogenous substrate by an enzyme related to Protein C anticoagulant activity; and (h) comparing the conversion rate of the exogenous substrate in blood sample to be analyzed with the conversion rate the exogenous substrate in a normal blood sample as determined by the method recited in steps (a)–(g).

2. The method according to claim 1, wherein the metal ion is $Mg^{2+}$ and the amount of the $Mg^{2+}$ ions added in step (d) is about 20 μmol to 10 mmol per liter of reaction mixture.

3. The method according to claim 1, wherein the metal ion is $Mg^{2+}$ and the amount of the $Mg^{2+}$ ions added in step (d) is about 100 μmol to 2 mmol per liter of reaction mixture.

4. The method according to claim 1, wherein the metal ion is $Mg^{2+}$ and the amount of the $Mg^{2+}$ ions added in step (d) is about 200 μmol to 1 mmol per liter of reaction mixture.

5. The method according to claim 1, wherein the amount of $Mn^{+2}$, $Zn^{+2}$, $Ni^{+2}$, $Sr^{+2}$, $Cu^{+2}$, or $Cu^{+}$ ions added in step (d) is about 1 μmol to 2 mmol per liter of reaction mixture.

6. The method according to claim 1, wherein the amount of $Mn^{+2}$, $Zn^{+2}$, $Ni^{+2}$, $Sr^{+2}$, $Cu^{+2}$, or $Cu^{+}$ ions added in step (d) is about 5 μmol to 400 μmol per liter of reaction mixture.

7. The method according to claim 1, wherein the amount of $Mn^{+2}$, $Zn^{+2}$, $Ni^{+2}$, $Sr^{+2}$, $Cu^{+2}$, or $Cu^{+}$ ions added in step (d) is about 10 μmol to 80 μmol per liter of reaction mixture.

8. The method according to claim 1, wherein the exogenous substrate added in step (e) is a substrate for a component of the coagulation cascade selected from the group consisting of Factor Xa and thrombin.

9. The method according to claim 8, wherein the substrate added in step (e) is a substrate for Factor Xa selected from the group consisting of Benzoyl-Ile-Glu-Gly-Arg-pNA, N-a-Z-D-Arg-Gly-Arg-pNA, $CH_3SO_2$-D-Leu-Gly-Arg-pNA, and MeO-CO-D-CHG-Gly-Arg-pNA.

10. The method according to claim 8, wherein the substrate added in step (e) is a substrate for thrombin selected from the group consisting of H-D-Phe-Pip-Arg-pNA, pyroGlu-Pro-Arg-pNA, H-D-Ala-Pro-Arg-pNA, Z-D-Arg-Sarc-Arg-pNA, AcOH*H-D-CHG-But-Arg-pNA, and H-D-HHT-Ala-Arg-pNA.

11. The method according to claim 1, wherein said exogenous substrate includes a photometrically measurable leaving group.

12. The method according to claim 11, wherein the photometric substrate includes a leaving group selected from the group consisting of a chromophore, a fluorophore, and a luminophore.

13. The method according to claim 12, wherein the photometric substrate comprising a p-nitroaniline group (pNA) as a chromophoric leaving group.

14. The method according to claim 12, wherein the photometric substrate comprises a naphthylamine or coumarine derivative group as a fluorophoric leaving group.

15. The method according to claim 12, wherein the photometric substrate comprises an isoluminolamide group as a luminophoric leaving group.

16. The method according to claim 1, wherein the blood sample is selected from the group consisting of whole blood, blood plasma, and blood serum.

17. The method according to claim 1, wherein the activating, triggering, and adding steps occur separately.

18. The method according to claim 1, wherein the activating, triggering, and adding steps occur simultaneously.

19. The method according to claim 1, wherein the amount of calcium ions added in step (c) is about 0.5 mmol to 20 mmol per liter of reaction mixture.

20. The method according to claim 1, wherein the amount of calcium ions added in step (c) is about 1 mmol to 10 mmol per liter of reaction mixture.

21. The method according to claim 1, wherein the amount of calcium ions added in step (c) is about 200 μmol to 1 mmol per liter of reaction mixture.

22. The method according to claim 1, wherein the activating the coagulation cascade step occurs via the intrinsic pathway and the coagulation activator for the intrinsic pathway compositions comprises phospholipid(s) and contact activators.

23. The method according to claim 1, wherein the activating the coagulation cascade step occurs via the intrinsic pathway and the coagulation activator for the intrinsic pathway compositions comprises phospholipid(s) and an intrinsic pathway factor selected from the group consisting of Factor IXa, Factor XIIa, and Factor XIa.

24. The method according to claims 22–23, wherein the phospholipids are selected from the group consisting of synthetic phospholipids, purified phospholipids, and crude extracts of phospholipids derived from biological sources.

25. The method according to claim 1, wherein the activating the coagulation cascade step occurs via the intrinsic pathway and the coagulation activator for the intrinsic pathway compositions comprises phospholipid(s), contact activators, and an intrinsic pathway factor selected from the group consisting of Factors IXa, Factor XIIa, and Factor XIa.

26. The method according to claim 25, wherein the contact activator is selected from the group consisting of ellagic acid, collagen, collagen-related substances, and silica.

27. The method according to claim 25, wherein the contact activator is a silica selected from the group consisting selected from the group consisting of micronized silica, colloidal silica, and kaolin.

28. The method according to claim 1, wherein the activating the coagulation cascade step occurs via the extrinsic pathway and the coagulation activator for the extrinsic pathway is selected from native human tissue factor, recombinant human tissue factor, non-human native tissue factor, non-human recombinant tissue factor, native human Factor VII/VIIa, recombinant human Factor VII/VIIa, native non-human Factor VII/VIIa, and recombinant non-human Factor VII/VIIa.

29. The method according to claim 24, the phospholipids are selected from the group consisting of phosphatidylcholine, phosphatidylserine, and sphinogmyelin.

30. The method according to claim 1, wherein the activating the coagulation cascade step occurs via the common pathway and the coagulation activator is selected from the group consisting of exogenous Factor Xa, exogenous Factor X and an exogenous activator for Factor X, and an exogenous activator for endogenous Factor X.

31. The method according to claim 30, wherein the exogenous activator for Factor X is snake venom enzyme.

32. The method according to claim 31, wherein the exogenous activator for Factor X comprises Russelli Viperii snake venom enzyme.

33. The method according to claim 1, further comprising the step of adding components of the Protein C anticoagulant pathway to compensate for variable functional levels of the components of the anticoagulant pathway in the sample, said components being selected from the group consisting of Protein C, activated Protein C, Protein S, Factor V, Factor Va, a plasma deficient of the Protein C anticoagulant pathway component to be analyzed, and a plasma deficient of all components of the Protein C anticoagulant pathway.

34. The method according to claim 1, wherein a fibrin polymerization inhibitor is added to the blood sample to be analyzed.

35. The method according to claim 34, wherein the fibrin polymerization inhibitor is Gly-Pro-Arg-Pro.

36. The method according to claim 1, wherein the procoagulation reagent is selected from the group consisting of Factor VIII, Factor VIIIa, Factor IX, Factor X, and prothrombin.

37. The method of claim 1, wherein the component of the Protein C anticoagulant pathway analyzed is Protein C, said method further comprising the step of activating Protein C by adding exogenous activated Protein C to the blood sample to be analyzed.

38. The method according to claim 1, wherein the component of the Protein C anticoagulant pathway analyzed is Protein C, said method further comprising the step of activating Protein C by adding an activator of Protein C to the blood sample to be analyzed.

39. The method according to claim 1, wherein the component of the Protein C anticoagulant pathway analyzed is Protein C, said method further comprising the step of adding exogenous Protein C together with an activator of Protein C to the blood sample to be analyzed.

40. The method according to any one of claims 37–39, wherein the metal ions are added simultaneously with the Protein C activator.

41. The method according to any one of claims 37–39, wherein the activating Protein C step occurs simultaneously with activating the coagulation cascade step.

42. The method according to any one of claims 37–39, wherein the activating Protein C step precedes the activating the coagulation cascade step.

43. The method according to any one of claims 37–39, wherein the activator for Protein C comprises Protein C activating snake venom enzyme and thrombin.

44. The method according to any one of claims 37–39, wherein the activator for Protein C further comprises thrombomodulin.

45. The method according to any one of claims 37–39, wherein the Protein C activator is recombinant Protein C activator.

46. The method according to any one of claims 37–39, wherein the Protein C activating snake venom enzyme is obtained from the Agkistrodon family of Agkistrodon contortrix contortrix.

47. The method according to claim 46, wherein the snake venom enzyme is crude snake venom enzyme.

48. The method according to claim 46, wherein the snake venom enzyme is purified snake venom enzyme.

49. The method according to claim 48, wherein the amount of purified Protein C activator added is about $1\times10^{3}$ U to 1 U per milliliter of reaction mixture.

50. The method according to claim 48 wherein the amount of purified Protein C activator added is about $2\times10^{-3}$ U to 0.3 U per milliliter of reaction mixture.

* * * * *

UNITED STATES PATENT AND TRADEMARK OFFICE

CERTIFICATE OF CORRECTION

PATENT NO. : 6,395,501 B1
DATED : May 28, 2002
INVENTOR(S) : Rosen et al.

It is certified that error appears in the above-identified patent and that said Letters Patent is hereby corrected as shown below:

Column 26,
Line 43, after "of" insert -- $Mg^{+2}$, --;

Column 28,
Line 1, replace "24" with -- 25 -- and replace "22–23" with -- 23–24 --;
Lines 5 and 12, replace "25" with -- 24 --;
Line 16, replace "25" with -- 26 --;
Line 29, replace "24" with -- 25 -- and add -- wherein -- before "the phospholipids";
Lines 30-31, replace "sphinogmyelin" with -- sphingomyelin --;

Column 30,
Line 16, replace "$10^{3}$" with -- $10^{-3}$ --.

Signed and Sealed this

Twenty-eighth Day of October, 2003

JAMES E. ROGAN
*Director of the United States Patent and Trademark Office*